(12) United States Patent  
Killion et al.

(10) Patent No.: US 8,649,540 B2
(45) Date of Patent: Feb. 11, 2014

(54) ELECTRONIC EARPLUG

(75) Inventors: Mead C. Killion, Elk Grove Village, IL (US); Stephen Drake Julstrom, Chicago, IL (US); Timothy Scott Monroe, Schaumburg, IL (US); Viorel Drambarean, Skokie, IL (US)

(73) Assignee: Etymotic Research, Inc., Elk Grove Village, IL (US)

( * ) Notice: Subject to any disclaimer, the term of this patent is extended or adjusted under 35 U.S.C. 154(b) by 472 days.

(21) Appl. No.: 12/914,314

(22) Filed: Oct. 28, 2010

(65) Prior Publication Data

US 2011/0103605 A1 May 5, 2011

Related U.S. Application Data

(60) Provisional application No. 61/256,807, filed on Oct. 30, 2009, provisional application No. 61/298,755, filed on Jan. 27, 2010, provisional application No. 61/299,232, filed on Jan. 28, 2010, provisional application No. 61/313,201, filed on Mar. 12, 2010, provisional application No. 61/386,344, filed on Sep. 24, 2010.

(51) Int. Cl.
*H04R 25/00* (2006.01)

(52) U.S. Cl.
USPC ........................................................ 381/321

(58) Field of Classification Search
USPC ........................................................ 381/321
See application file for complete search history.

(56) References Cited

U.S. PATENT DOCUMENTS

| | | | |
|---|---|---|---|
| 3,894,195 A * | 7/1975 | Kryter | 381/23.1 |
| 4,592,087 A | 5/1986 | Killion | |
| 4,677,679 A | 6/1987 | Killion | |
| 4,689,819 A | 8/1987 | Killion | |
| 4,807,612 A | 2/1989 | Carlson | |
| 4,924,502 A | 5/1990 | Allen et al. | |
| 5,131,046 A | 7/1992 | Killion et al. | |
| 5,203,352 A | 4/1993 | Gardner, Jr. | |
| 5,279,292 A * | 1/1994 | Baumann et al. | 607/137 |
| 5,390,254 A * | 2/1995 | Adelman | 381/315 |
| 5,402,494 A * | 3/1995 | Flippe et al. | 381/314 |
| 5,479,522 A * | 12/1995 | Lindemann et al. | 381/23.1 |
| 5,553,152 A * | 9/1996 | Newton | 381/328 |

(Continued)

OTHER PUBLICATIONS http://www.walkersgameear.com/enhancement_hdSeries.html (printed on Oct. 28, 2010).

*Primary Examiner* — Alexander Jamal
(74) *Attorney, Agent, or Firm* — McAndrews, Held & Malloy, Ltd.

(57) ABSTRACT

Electronic earplugs, methods of enhancing and/or attenuating sound using electronic earplugs, and kits including electronic earplugs are provided. Certain electronic earplugs provided can deliver sound to a user's ear canal at levels below, equal to, and/or above ambient sound levels for specified ambient sound level ranges. Certain electronic earplugs provided can be switched between first and second settings with different sound level delivery settings. Certain electronic earplugs provided can be coupled with or integrated into two-way communication devices. Certain of such two-way communication devices can use induction to receive and transmit audio signals. Certain electronic earplugs provided can include a receive coil configured to allow remote radio signals to be received. Certain electronic earplugs provided can block at least about 35 dB of ambient sound when fully inserted into a user's ear canal. Kits that include electronic earplugs and accessories for use with electronic earplugs are also provided.

50 Claims, 22 Drawing Sheets

(56) References Cited

U.S. PATENT DOCUMENTS

| | | | |
|---|---|---|---|
| 5,600,728 A * | 2/1997 | Satre | 381/314 |
| 5,608,803 A * | 3/1997 | Magotra et al. | 381/314 |
| 5,623,550 A | 4/1997 | Killion | |
| 5,745,587 A * | 4/1998 | Statz et al. | 381/120 |
| 5,812,679 A | 9/1998 | Killion et al. | |
| 5,822,442 A * | 10/1998 | Agnew et al. | 381/107 |
| 5,838,807 A * | 11/1998 | Andersson et al. | 381/321 |
| 5,862,238 A * | 1/1999 | Agnew et al. | 381/321 |
| 5,936,208 A | 8/1999 | Hamery | |
| 6,041,129 A * | 3/2000 | Adelman | 381/328 |
| 6,047,075 A | 4/2000 | Killion et al. | |
| 6,320,969 B1 | 11/2001 | Killion | |
| 6,466,678 B1 | 10/2002 | Killion et al. | |
| RE38,351 E | 12/2003 | Iseberg et al. | |
| 6,694,034 B2 | 2/2004 | Julstrom et al. | |
| 6,704,424 B2 | 3/2004 | Killion | |
| 7,099,486 B2 | 8/2006 | Julstrom et al. | |
| 7,206,426 B1 | 4/2007 | Julstrom et al. | |
| 7,522,740 B2 | 4/2009 | Julstrom et al. | |
| 7,853,029 B2 * | 12/2010 | Jensen | 381/312 |
| 8,041,227 B2 * | 10/2011 | Holcombe et al. | 398/138 |
| 8,340,338 B2 * | 12/2012 | Mlodzikowski et al. | 381/380 |
| 2008/0311966 A1 * | 12/2008 | Klein | 455/575.2 |
| 2010/0061576 A1 | 3/2010 | Johnson et al. | |
| 2011/0228947 A1 * | 9/2011 | Killion et al. | 381/72 |

\* cited by examiner

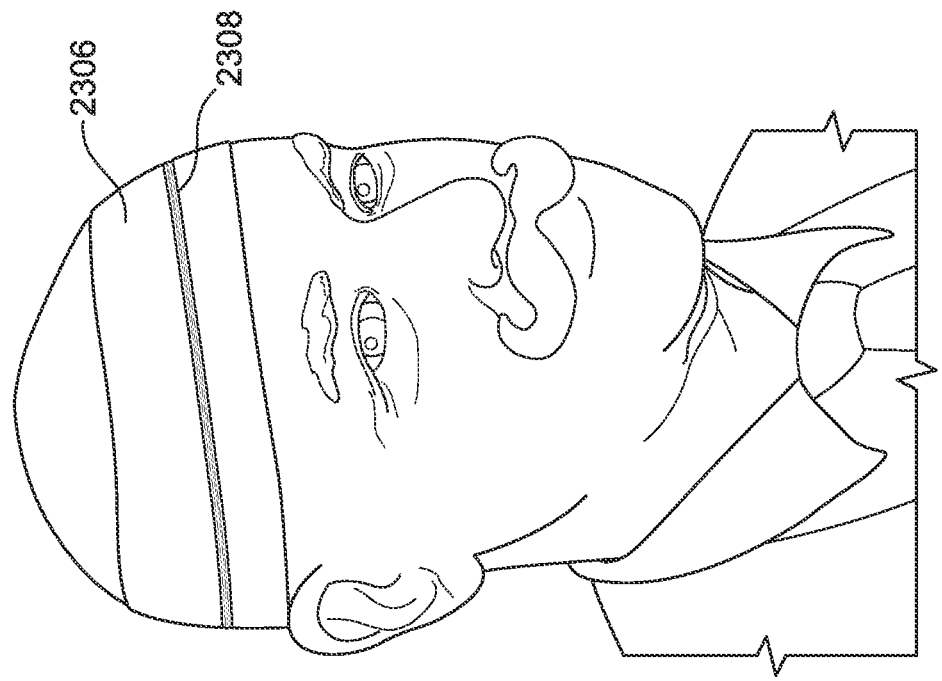
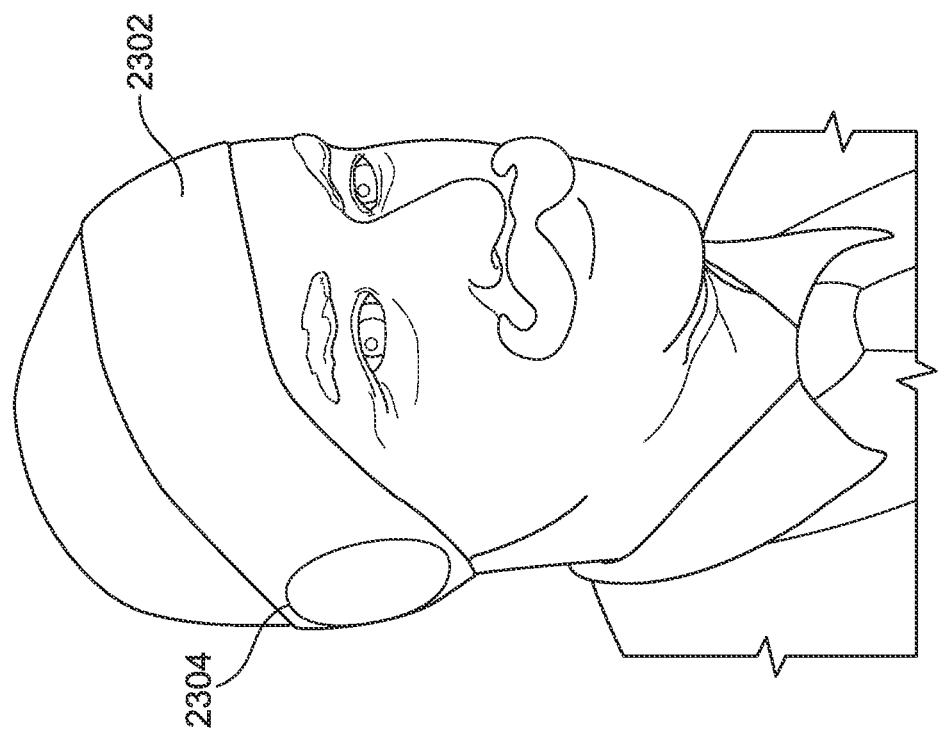

ELECTRONIC EARPLUG

CROSS-REFERENCE TO RELATED APPLICATIONS/INCORPORATION BY REFERENCE

This application claims priority to the following U.S. Provisional Applications: 61/256,807 filed Oct. 30, 2009 entitled Electronic Earplug; 61/298,755 filed Jan. 27, 2010 entitled Electronic Earplug; 61/299,232 filed Jan. 28, 2010 entitled Two-Way Communication Device With Multiple Microphones; 61/313,201 filed Mar. 12, 2010 entitled Telecoil Option For Electronic Blast Plug And Quiet Sound Amplifier Products; and 61/386,344 filed Sep. 24, 2010 entitled Wireless Two-Way Communication Device Using A Single Coil, which provisional applications are incorporated by reference herein in their entirety.

U.S. Pat. No. 4,592,087 issued to Killion on May 27, 1986, is incorporated by reference herein in its entirety.

U.S. Pat. No. 4,677,679 issued to Killion on Jun. 30, 1987, is incorporated by reference herein in its entirety.

U.S. Pat. No. 4,689,819 issued to Killion on Aug. 25, 1987, is incorporated by reference herein in its entirety.

U.S. Pat. No. 5,131,046 issued to Killion et al. on Jul. 14, 1992, is incorporated by reference herein in its entirety.

U.S. Pat. No. 5,623,550 issued to Killion et al. on Apr. 22, 1997, is incorporated by reference herein in its entirety.

U.S. Pat. No. 5,812,679 issued to Killion et al. on Sep. 22, 1998, is incorporated by reference herein in its entirety.

U.S. Pat. No. 6,047,075 issued to Killion et al. on Apr. 4, 2000, is incorporated by reference herein in its entirety.

U.S. Pat. No. 6,320,969 issued to Killion et al. on Nov. 20, 2001, is incorporated by reference herein in its entirety.

U.S. Pat. No. 6,466,678 issued to Killion et al. on Oct. 15, 2002, is incorporated by reference herein in its entirety.

U.S. Pat. No. RE 38,351 issued to Iseberg et al. on Dec. 16, 2003, is incorporated by reference herein in its entirety.

U.S. Pat. No. 6,694,034 issued to Julstrom et al. on Feb. 17, 2004, is incorporated by reference herein in its entirety.

U.S. Pat. No. 6,704,424 issued to Killion et al. on Mar. 9, 2004, is incorporated by reference herein in its entirety.

U.S. Pat. No. 7,099,486 issued to Julstrom et al. on Aug. 29, 2006, is incorporated by reference herein in its entirety.

U.S. Pat. No. 7,206,426 issued to Julstrom et al. on Apr. 17, 2007, is incorporated by reference herein in its entirety.

U.S. Pat. No. 7,522,740 issued to Julstrom et al. on Apr. 21, 2009, is incorporated by reference herein in its entirety.

U.S. Pat. No. 6,694,034 issued to Julstrom et al. on Feb. 17, 2004 is incorporated by reference herein in its entirety.

U.S. patent application Ser. No. 12/207,317, by Johnson et al., published Mar. 11, 2010 as U.S. App. Pub. No. 2010/0061576 is incorporated by reference herein in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

It is highly documented that military personnel exposed to blasts from firearms, explosions and other high level peak noises are at high risk for hearing loss. It has been estimated that 68% of deployed soldiers return with ear damage, and 100% do not protect both ears during combat. (Saunders and Griest, "Hearing loss in veterans and the need for hearing loss prevention programs" NHCA Meeting, Portland Oreg., Feb. 23, 2008). In 2007, it was estimated that the cost of hearing aids for soldiers was $141.3 million and the cost for clinical services (not including hearing aids) was $147.1 million. (Saunders and Griest, "Hearing loss in veterans and the need for hearing loss prevention programs" NHCA Meeting, Portland Oreg., Feb. 23, 2008).

Sound pressure levels (SPLs) over 160 dB that occur over periods as short as even a few milliseconds are sufficient to cause damage to the unprotected ear. Exposure to the peak noises caused by gunfire or other explosions adds hearing loss to the long list of risks and dangers encountered by soldiers on the battle field. One means to prevent hearing loss is to wear a noise attenuating device such as ear plugs or earmuffs. U.S. Pat. No. 5,203,352 issued to Gardner presents high-attenuation foam earplugs which may provide up to 40 dB of attenuation when properly inserted. Accordingly, the Gardner earplugs will reduce hazardous external peak SPLs of 160 to 190 dB to safer levels of 120 to 150 dB, respectively, within the ear canal of the wearer.

The Gardner and other similar earplugs will attenuate up to 40 dB of noise, but the attenuation level is independent of the level external sound. In other words, all external noises will be attenuated the same amount whether the sounds are extremely loud or very soft. Thus, softer sounds that would otherwise be audible without the use of earplugs may become inaudible or become so soft that they go unnoticed. For many work environments the perception of soft sounds is vital to the task at hand or the safety of the workers. For example, a soldier wearing earplugs as described attenuating a constant 40 dB of noise may fail to hear an enemy quietly approaching or fail to perceive communications from fellow soldiers. Likewise, a construction worker wearing such earplugs may receive adequate protection from high level construction sounds, but fail to hear a distant coworker's emergency call for help.

Many earplugs, like those described by Gardner, for example, may distort the reception of normal sound. The earplugs attenuate higher frequency sounds at a higher level than lower frequency sounds making it difficult for the wearer to hear or understand speech and other important sounds. High-audibility earplugs such as those described by U.S. Pat. No. 4,807,612 issued to Carlson and used in the ER-9®, the ER-15®, and the ER-25® series Musicians Earplugs® produced by Etymotic Research, Inc., and having nominal 9 dB, 15 dB, and 25 dB attenuation respectively, and as described in U.S. Pat. No. 5,113,967 issued to Killion et al., and used in products such as the ER-20® series HiFi earplugs produced by Etymotic Research, Inc.®, all produce relatively uniform attenuation across audible frequency ranges and a low enough attenuation such that speech and music remain highly audible to the wearer. While the high audibility of these earplugs allows the wearer to hear softer noises, they may not provide adequate protection for extremely high level sounds. Moreover, even the lowest-attenuation ER-9 earplug may produce unacceptable attenuation for a soldier who needs to have the best chance of hearing a quietly approaching enemy. Moreover 9 dB attenuation is insufficient to protect the soldier's ears from many high-energy noise levels that occur during battle.

An earplug with sound level dependent attenuation is described in U.S. Pat. No. 4,924,502 issued to Allen, et al. and U.S. Pat. No. 5,936,208 issued to Hamery and is embodied in a product sold by AEARO Technologies under the trade name Combat Arms Earplug. The Combat Arms Earplug introduces less noise attenuation for external SPLs below 110 dB than for external SPLs above 110 dB, but does not provide a constant attenuation across all frequencies. For example, where the external SPL is below 110 dB the Combat Arms Earplug provides around 5 dB of attenuation at very low frequencies and up to 23 dB attenuation at higher frequencies. Where the external SPL is above 110 dB, the attenuation provided increases by approximately 0.3 dB for each 1 dB increase of external sound until a maximum level of attenuation is achieved. For example a 9 dB change for 110-150 input gives 9/40=0.23 dB/dB. For the 150-190 range, the attenuation may increase another 12 dB in that 40 dB range, or 0.3 dB/dB. The Combat Arms Earplug provides a passageway that allows partially unobstructed travel of sound from the exterior into the ear canal with a relatively low level of attenuation at low sound pressure levels. A sharp obstruction located within the passageway of the Combat Arms Earplug causes the flow of sound within the earplug to become turbulent above 110 dB. This introduction of turbulent flow impedes the flow of the sound into the ear, thereby establishing greater attenuation. While the aforementioned earplugs may provide non-linear pattern attenuation, they do not provide enough audibility for low-level sounds: The 15-23 dB attenuation they provide between 1 kHz and 3 kHz (Berger and Hamery "Empirical evaluation using impulse noise of the level-dependency of various passive earplug designs;" Presentation at Acoustics Paris 2008 J. Acoust Soc. Am. 123 (5, Pt. 2), p. 3528) is apparently too much to provide good situation awareness for the soldier. As a result, "Many troops say they don't use hearing protection on missions because they feel it affects their situational awareness, ability to do their jobs and complete their missions" according to Dr. Joseph Brennan in an Army Times staff report "Troops reject ear protection in Afghanistan" Posted: Wednesday Aug. 26, 2009 5:29:32 EDT. Other estimates are that 68% of deployed soldiers return with ear damage, and the majority refuse to wear earplugs, costing some $288 million each year in auditory rehabilitation (Saunders and Griest, "Hearing loss in veterans and the need for hearing loss prevention programs" NHCA Meeting, Portland Oreg., Feb. 23, 2008).

It seems clear from the refusal of soldiers to wear existing hearing protection that no existing devices provide the combination of situational awareness (especially for quiet sounds) and blast protection that is needed.

Electronic hearing protection would appear to be a better solution, and indeed has also been known for many years. A popular form is the "Walker Game Ear" device. This and similar forms typically provide some gain for quiet sounds under the assumption that the typical hunter purchaser already has some hearing loss so that a combination hearing aid and hearing protection would be beneficial. They all have in common that they use a tiny hearing aid receiver whose maximum output of 110-125 dB is further limited by a limited power available from the output amplifier in the hearing aid. Thus the peak pressure from a firearm of typically or 170 dB is reduced to a snap of less than 130 dB, which is safe for the 1 or 2 milliseconds of the pulse duration. According to Berger, firearms, howitzers and roadside explosions typically fall in the range of 150 to 180 dB SPL. This electronic approach is well known to the applicant, since the "K-AMP" hearing aid (which was designed by Etymotic Research, described in U.S. Pat. No. 5,131,046, and manufactured by nearly every hearing aid company in the 1990s) was used for hearing protection by many including one of its own employees while hunting. The K-AMP Hearing Aid had the advantage that it provided normal localization for the hunter and near-normal "situational awareness," but a drawback was that it had to be built into a custom earmold shell which typically required 2-3 visits to a licensed hearing aid dispenser.

The problem with all present devices is that they do not provide a low-cost, ready-to-wear, high-fidelity device with a 16 kHz bandwidth, suitable for the normal-hearing soldier. The lack of understanding that this is even possible is indicated perhaps by the fact that in many pages of Army "SBIR" requests for proposals perused by the applicant, none of them describe the type of device that the applicant has developed, or apparently even imagined that it was possible.

SUMMARY OF THE INVENTION

Certain embodiments of the present technology provide electronic earplugs, methods of enhancing and/or attenuating sound using electronic earplugs, and kits including electronic earplugs.

In an embodiment, an electronic earplug includes: a microphone configured to convert ambient sound to input electrical signals; a circuit operatively connected to the microphone, the circuit configured to receive the input electrical signals from the microphone and provide output electrical signals to a receiver, the circuit configured to modify a sound output level from the electronic earplug to a user's ear canal based on a sound input level of the ambient sound, wherein the circuit is configured such that for sound input levels between a first value and a second value, the sound output level is about equal to the sound input level; and the receiver operatively connected to the circuit, the receiver configured to convert the output electrical signals into sound that is communicated to the user's ear canal.

In an embodiment, the circuit is configured such that for sound input levels between the second value and a third value that is greater than the second value, the sound output level is equal to about the second value.

In an embodiment, the second value is about 105 dB SPL or about 115 dB SPL.

In an embodiment, the circuit is configured to reduce the second value by about 10 dB using a resistor across terminals of the receiver.

In an embodiment, the circuit is configured such that for sound input levels between the first value and a third value that is less than the first value, the sound output level is greater than the sound input level.

In an embodiment, the circuit is configured such that for sound input levels between the first value and a third value that is less than the first value, the sound output level is less than the sound input level.

In an embodiment, the circuit is configured such that it can be switched between a first setting and a second setting, the first setting having the sound output level be about equal to the sound input level for inputs up to about the first value, the second setting having the sound output level be greater than the sound input level for inputs up to about the first value.

In an embodiment, the circuit is configured such that it can be switched between the first setting and the second setting by throwing a single pole single throw switch in series with a threshold knee controlling portion of the circuit.

In an embodiment, the circuit is configured such that it can be switched between a first setting and a second setting, the first setting having the sound output level be greater than the sound input level for inputs up to about the first value, the second setting having the sound output level be less than the sound input level for at least one input below the first value.

In an embodiment, the circuit is configured such that it can be switched between the first setting and the second setting by throwing a single pole double throw switch to select two different volume control resistors.

In an embodiment, the electronic earplug further includes an eartip configured to block at least about 35 dB of the ambient sound when the eartip is received in the user's ear canal.

In an embodiment, the circuit includes a battery polarity reversing circuit configured to detect the polarity of a battery and reverse polarity based on the orientation of the battery.

In an embodiment, the circuit includes a Class B output.

In an embodiment, the circuit includes a circuit configured to signal when battery power is below a certain level.

In an embodiment, the microphone is blast resistant.

In an embodiment, the electronic earplug is fully supported by the ear canal.

In an embodiment, the electronic earplug is configured to be coupled with a two-way wireless communication device such that signals received from the two-way wireless communication device are communicated to the electronic earplug.

In an embodiment, the electronic earplug is configured to be coupled with a two-way wireless communication device such that signals received at a microphone configured to receive audible cues from the wearer of the electronic earplug are transmitted from the two-way wireless communication device.

In an embodiment, the electronic earplug further includes a receive coil configured to be magnetically coupled with a remote transmit coil such that signals received from the remote transmit coil are communicated to the electronic earplug.

In an embodiment, the signals received from the remote transmit coil are not amplified or attenuated by the circuit prior to being converted to sound for delivery using the electronic earplug.

In an embodiment, the receive coil includes a long axis that extends substantially parallel to a sound channel configured to deliver sound to a user's ear canal such that the receive coil remains similarly oriented relative to the user's ear canal when the electronic earplug is rotated in the user's ear canal.

In an embodiment, the electronic earplug includes an exterior facing end that is disposed opposite the user's ear canal when the electronic earplug is being worn, and wherein the microphone is configured to receive ambient sound through an inlet disposed on the exterior facing end.

In an embodiment, the electronic earplug includes an exterior facing end that is disposed opposite the user's ear canal when the electronic earplug is being worn, and wherein the microphone is configured to receive ambient sound through an inlet disposed on a side of the electronic earplug that is not the exterior facing end.

In an embodiment, electronic earplug of claim 1, further includes a receive coil configured to inductively receive a first audio signal from a radio interface loop, the first audio signal being communicated from a two-way communication device operably connected to the radio interface loop; and a transmit coil configured to generate a second audio signal, wherein the radio interface loop is configured to inductively receive the second audio signal and communicate the second audio signal to the two-way communication device.

In an embodiment, the transmit coil is configured to generate the second audio signal based on sound received at a boom microphone extending from a headset that includes the electronic earplug.

In an embodiment, the second audio signal is coupled as an FM signal, and wherein the radio interface loop is connected to the two-way communication device via a radio interface module comprising a high-pass filter configured to filter the second audio signal and an FM demodulator configured to demodulate the second audio signal.

In an embodiment, the FM signal has a center frequency of about 100 kHz.

In an embodiment, the radio interface module is configured such that the second audio signal is filtered using the high pass filter before the second audio signal is demodulated using the FM demodulator.

In an embodiment, the first audio signal is a baseband audio signal, and wherein the radio interface loop is connected to the two-way communication device via a radio interface module comprising a low pass filter configured to filter the first audio signal.

In an embodiment, the two-way communication device is a two-way radio.

In an embodiment, a kit includes: an electronic earplug battery; a damper removal tool; and an electronic earplug comprising: a microphone configured to convert ambient sound to input electrical signals; a circuit operatively connected to the microphone, the circuit configured to receive the input electrical signals from the microphone and provide output electrical signals to a receiver, the circuit configured to modify a sound output level from the electronic earplug to a user's ear canal based on a sound input level of the ambient sound; the receiver operatively connected to the circuit, the receiver configured to convert the output electrical signals into sound that is communicated to the user's ear canal; a sound channel configured to communicate sound to the user's ear canal; and an acoustic damper disposed in the sound channel.

In an embodiment, the kit further includes a headband.

In an embodiment, the kit further includes an eartip.

In an embodiment, the kit further includes a pouch configured to store the other kit items.

In an embodiment, the kit further includes a second electronic earplug.

BRIEF DESCRIPTION OF THE DRAWING(S)

FIG. 22B depicts a user of an electronic earplug wearing a headband configured to provide an improved magnetic field at a receive coil disposed in the electronic earplug.

FIG. 22C depicts a user of an electronic earplug wearing a headband configured to provide an improved magnetic field at a receive coil disposed in the electronic earplug.

Figure 1:
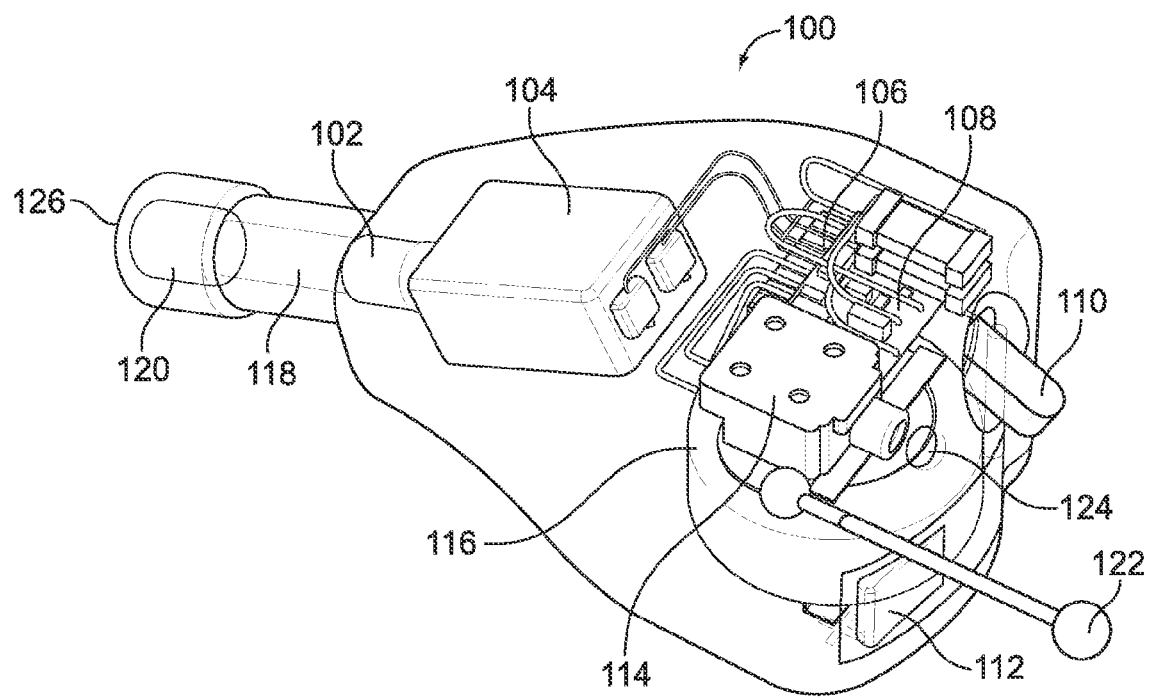
FIG. 1 depicts an electronic earplug used in accordance with embodiments of the present technology.

The foregoing summary, as well as the following detailed description of embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF PREFERRED EMBODIMENT(S)

Embodiments of the present technology provide electronic earplugs, methods of enhancing and/or attenuating sound using electronic earplugs, and kits including electronic earplugs.

The realization that it would be practical to make such a device came partly from considering experiments performed at the request of applicant's company by E-A-R Cal Laboratories. These experiments found that the attenuation of both foam eartips and triple-flange eartips, when combined with a miniature insert earphone such as the Etymotic ER-4 or ER-6i, was equal to or perhaps a dB or so greater than the attenuation of the foam or triple-flange eartip itself (which is normally manufactured without the sound channel down through the middle). Thus with the applicant's well-designed Electronic BlastPLG™ earplug, a protection of about 35 dB or more can be expected with fully inserted eartips for high-intensity sounds in the 160-180 dB SPL range, combined with near-normal situational awareness for all sounds below 105 or 115 dB SPL.

In the past a high fidelity or transparent frequency has been made practical in one of two ways: (1) use of an acoustic damping resistance and suitably chosen sound channel dimensions to mimic the frequency response of the ear as described in the above mentioned U.S. Pat. No. 5,131,046, which describes an embodiment of the K-AMP circuit; or (2) a sophisticated digital filtering method whereby the resonant peaks in the hearing aid receiver and the sound channel are compensated electronically by inverse filtering as in U.S. Pat. No. 6,466,678 for the Digi-K design. The lowest cost and thus most attractive approach for an initial electronic transparent blast plug appeared to be to adapt the method used in the Etymotic high fidelity earphones: use a replaceable damping filter which also served as a wax filter. The replacement design is useful in a practical device, because perhaps 10% of wearers will exude enough earwax to clog the device and keep the sound from coming out. A pair of replacement dampers and a damper replacement tool is included as described in U.S. Pat. No. RE 38,351 with each of the earphones, and can be included in the electronic blast protector so that if the soldier clogs one of the sound outlets with earwax, he can rapidly replace the damper and be back on the air. In an emergency, he can quickly pop the damper out with a sharp point to restore audibility, replacing it back at camp with a fresh damper to restore complete sound quality.

FIG. 1 depicts an electronic earplug 100 used in accordance with embodiments of the present technology. The electronic earplug 100 includes a sound tube 102, a receiver 104, a hybrid circuit 106, a battery polarity reversing circuit 108, a switch 110, a battery compartment 112, a microphone 114, a battery 116, a sound channel 118, an acoustic damper 120, and a removal string 122.

The electronic earplug 100 is configured to receive sound at microphone 114 through inlet port 124. Inlet port 124 is disposed on electronic earplug 100 on a wall opposite sound outlet 126. Sound outlet 126 is configured to deliver sound to a user's ear canal. Switch 110 and removal string 122 are also configured such that they extend from the wall opposite the sound outlet 126, which is the exterior facing end of the electronic earplug when in use. Such positioning can make switch 110 and removal string 122 accessible when electronic earplug 100 is in use.

The microphone 114 can be a blast-resistant microphone. The microphone 114 can convert sound to electrical signals. The electrical signals can be communicated to hybrid circuit 106, which can modify the sound level as discussed below, and pass electrical signals to the receiver 104. The receiver 104 can be a high fidelity receiver. The receiver 104 can convert the electrical signals to sound. The sound can be communicated from the receiver 104 to the sound coupling tube 102. The sound coupling tube 102 can be a vibration isolating tube to prevent mechanical feedback to the receiver 104. Sound can then be communicated via the sound channel 118, which can be a 16 kHz bandwidth sound channel, for example, to acoustic damper 120, which is disposed in the sound channel. The damper 120 can be removable and replaceable, can smooth frequency response, and can also act as a wax filter. Sound can then be communicated to the ear canal via sound outlet 126.

Figure 2:
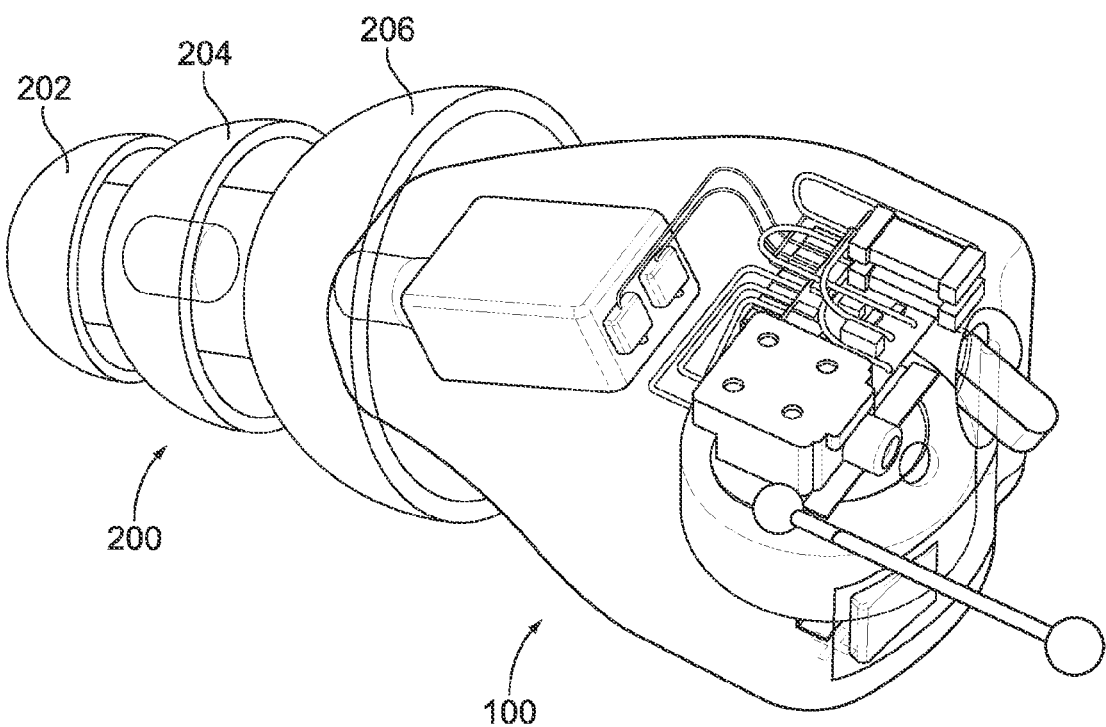
FIG. 2 depicts the electronic earplug of FIG. 1 with an eartip disposed thereon.
Figure 3:
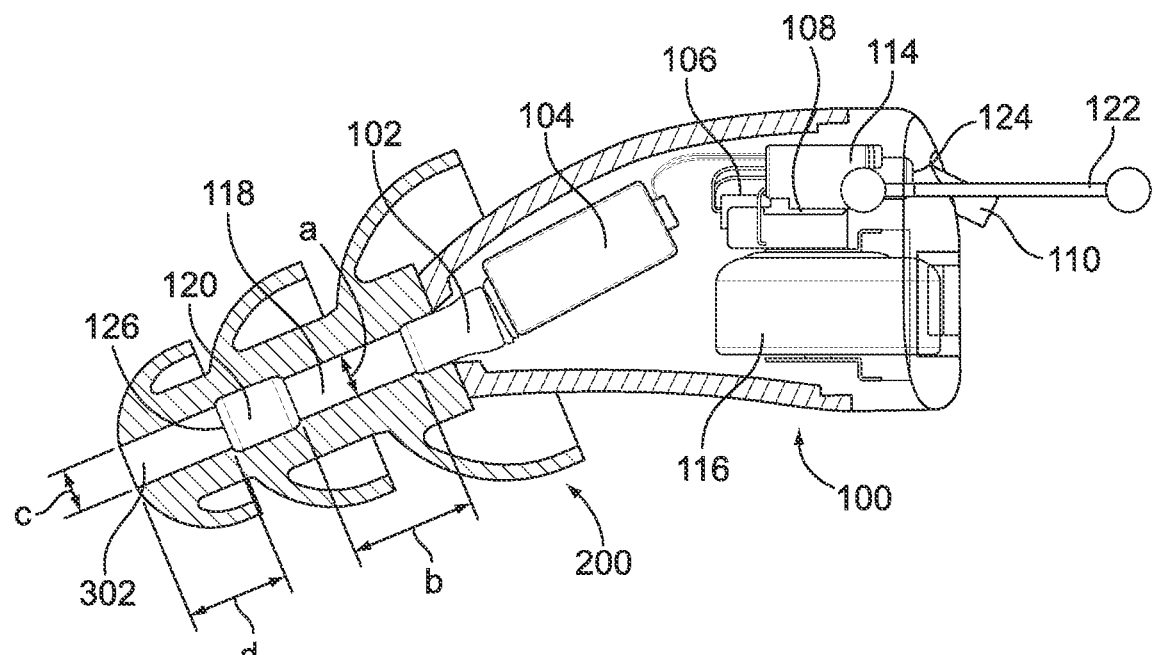
FIG. 3 depicts a cross section of the electronic earplug of FIG. 2.
Figure 4:
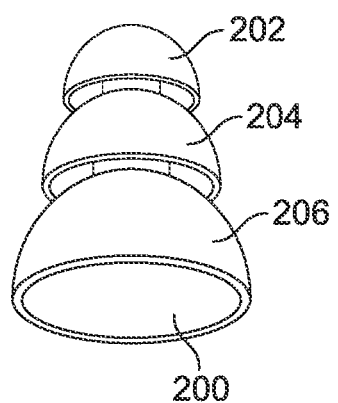
FIG. 4 depicts an eartip used in accordance with embodiments of the present technology.
Figure 5:
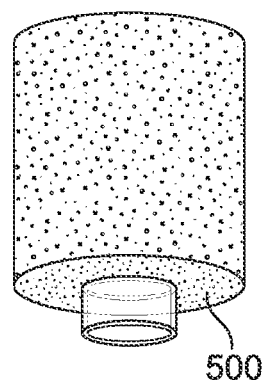
FIG. 5 depicts an eartip used in accordance with embodiments of the present technology.
Figure 6:
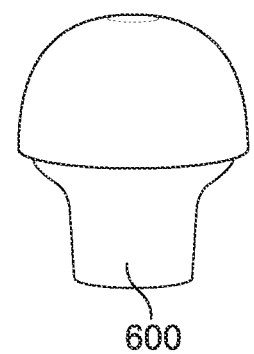
FIG. 6 depicts an eartip used in accordance with embodiments of the present technology.

FIG. 2 depicts electronic earplug 100 with an eartip 200 disposed thereon. FIG. 3 depicts a cross section of the electronic electronic earplug 100 and an example eartip 200. Eartip 200 comprises three concentric circular flanges 202, 204, 206, and is also shown in FIG. 4. Flanges 202, 204, 206 have increasing diameters, such that flange 202 is the smallest, flange 206 is the largest and flange 204, therebetween, is an intermediate size. When inserted into a user's ear canal, flange 202 enters first, and when fully inserted eartip 200 can block exterior noise up to about 35 dB or more from entering the ear canal. Such eartips can come in other forms, including those shown in FIGS. 5-6. FIG. 5 depicts a cylindrical foam eartip 500. FIG. 6 depicts a mushroom shaped foam eartip 600. Eartips 500 and 600 can have internal sound channel characteristics similar to those described below in connection with eartip 200.

As shown in FIG. 3, eartip 200 includes a channel 302 configured to receive electronic earplug 100 and to communicate sound from sound outlet 126 of electronic earplug 100 to the ear canal. Sound channel 302 in eartip 200 is preferably larger in diameter than sound channel 118 in electronic earplug 100, in order to improve high-frequency response. As shown in FIG. 3, for example, a suitable combination of dimensions for sound channel 118 is a diameter (indicated as a in FIG. 3) of about 1.55 milimeters (about 0.061 inches), and a length between sound tube 102 and damper 120 (indicated as b in FIG. 3) of about 4.34 milimeters (about 0.1709 inches). As also shown in FIG. 3, for example, a suitable combination of dimensions for sound channel 302 is a diameter (indicated as c in FIG. 3) of about 1.85 milimeters (about 0.073 inches), and a length from damper 120 to the end of eartip 200 (indicated as d in FIG. 3) of about 3.63 milimeters (about 0.143 inches). In an embodiment, a suitable combination of dimensions for the total sound path is as follows: about 0.080" long by about 0.042" diameter for sound tube 102, about 0.150" long by about 0.060" diameter for sound channel 118, and about 0.150" long by about 0.070" diameter for sound channel 302. The embodiments above can result in a "horn" action that provides the desired response out to 16 kHz, which would otherwise be deficient at the higher frequencies.

Electronic earplug 100 also includes switch 110 that can be used to turn electronic earplug 100 on or off. In certain embodiments, instead of simply turning electronic earplug 100 on and off, switch 110 can include various on positions, including one that does not provide any gain, and one that can provide a boost, such as a 15 dB boost, for quiet sounds (for example, sounds up to about 60 dB SPL). In an embodiment, one on position can provide for 15 dB attenuation for loud sounds (for example, sounds over about 90 dB SPL).

Sound control can be provided using hybrid circuit 106. That is, hybrid circuit 106 can modify the sound output level communicated to a user's ear canal based on the sound input level received at the electronic earplug microphone 114. Certain embodiments can include a hybrid circuit similar to those taught, for example, in the following U.S. patents and published applications: U.S. Pat. No. 5,131,046 issued to Killion et al. on Jul. 14, 1992; U.S. App. Pub. No. 2010/0061576 by Johnson et al.; U.S. Pat. No. 5,812,679 issued to Killion et al. on Sep. 22, 1998; U.S. Pat. No. 6,047,075 issued to Killion et al. on Apr. 4, 2000; and/or U.S. Pat. No. 6,466,678 issued to Killion et al. on Oct. 15, 2002.

Figure 7:
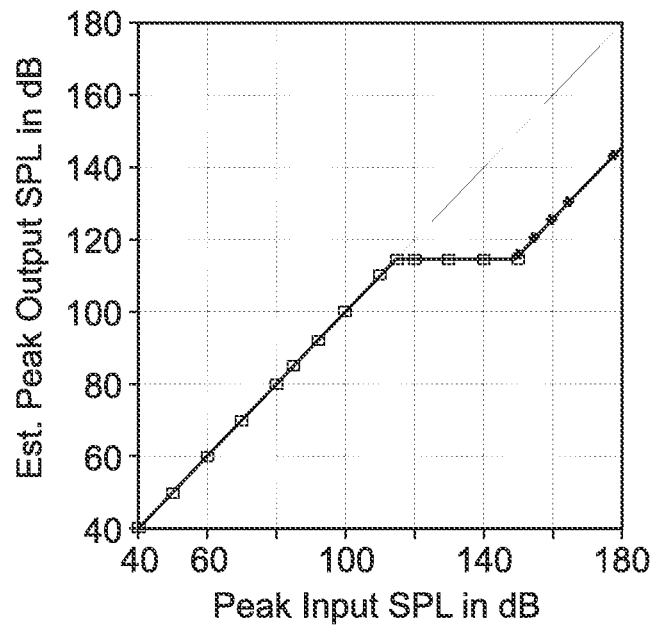
FIG. 7 is a graph depicting peak sound pressure level received at an electronic earplug vs. peak sound pressure level delivered to a user's ear canal for an electronic earplug used in accordance with embodiments of the present technology.

FIG. 7 is a graph depicting peak sound pressure level received at an electronic earplug vs. peak sound pressure level delivered to a user's ear canal for an electronic earplug used in accordance with embodiments of the present technology. As depicted in FIG. 7, an electronic earplug can be configured to provide no gain and no attenuation up to about 115 dB SPL. In other words, up to about 115 db SPL sound is delivered to the user's ear canal via the electronic earplug at the same dB SPL that sound is received at the electronic earplug microphone. For sound input levels between about 115 dB SPL and about 150 dB SPL, sound is delivered to the user's ear canal via the electronic earplug at about 115 dB SPL. In other words, sound received at the electronic earplug between about 115 dB SPL and about 150 dB SPL is delivered to the user's ear canal at a constant sound level of about 115 dB SPL. For sound input levels above 150 dB SPL, the level of sound in the ear canal is determined by the effective noise isolation provided by the electronic earplug/eartip. In other words, sound received at the electronic earplug above about 150 dB SPL is not primarily delivered to the user's ear canal via the electronic earplug circuitry. Rather, sound reaches the user's ear canal despite the electronic earplug being in place. The triple flange eartips typically provide about 35 dB of attenuation, the amount depicted in FIG. 7. Deeply inserted foam eartips typically provide about 40 dB of attenuation. A foam eartip deeply inserted in a steel-walled ear simulator such as the Zwislocki coupler, can provide 50 dB of attenuation, as illustrated by the data in FIG. 8. In all cases, the eartip should preferably be deeply sealed in the ear canal to obtain the stated attenuation. Electronic earplugs configured to perform as depicted in FIG. 7 can provide sound without gain or attenuation up to about 115 dB SPL and hearing protection over 115 dB SPL.

Figure 8:
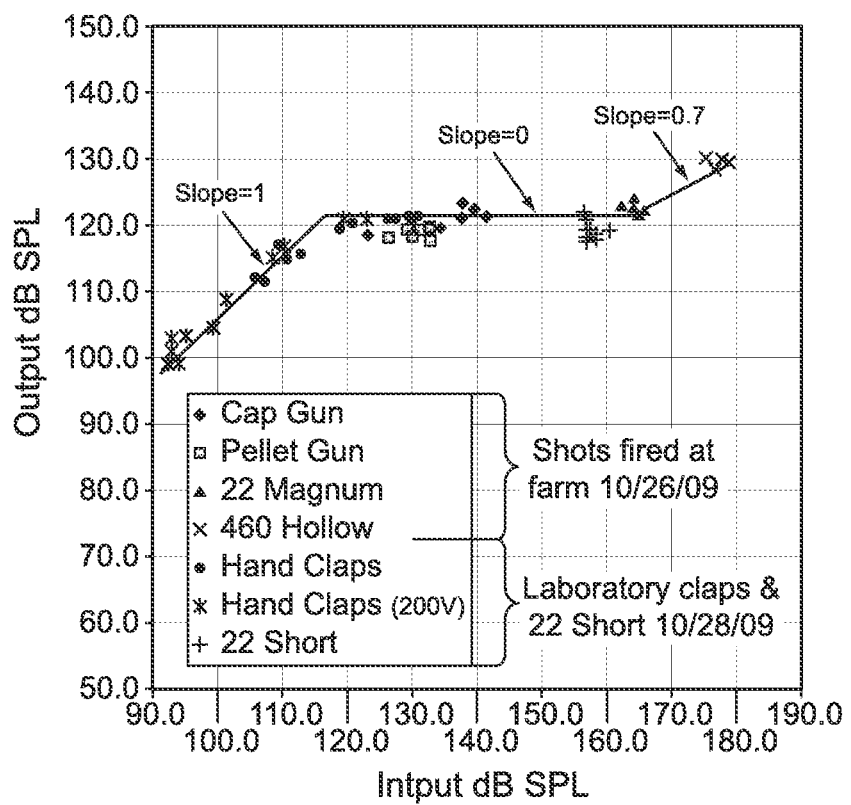
FIG. 8 is a graph depicting test results for a prototype electronic earplug used in accordance with embodiments of the present technology.

FIG. 8 is a graph depicting test results for a prototype electronic earplug configured to perform as described in FIG. 7. The graph depicts input dB SPL vs. output dB SPL for hand claps, louder hand claps, a cap gun, a pellet gun, and three pistols: a 22 Short, a 22 Magnum, and a 460 Hollow. During the tests, the sound into and out of an inventive electronic blast protection earplug was measured. The sound into the electronic earplug is the sound that would be experienced exterior to the ear, and the sound out of the electronic earplug is the sound that would be experienced in the ear canal. Both the input SPL and output SPL data represent (oscilloscope) peak eardrum-pressure equivalent data. Applying a standard diffuse-field-inverse filter, as is well known to be useful to relate ear canal SPL data to normally obtained sound field damage risk data, would reduce the measured output SPL numbers in FIG. 8 approximately 5 dB.

In FIG. 8 the input SPL is measured in front of a Zwislocki Coupler ear simulator, while the output SPL is measured at the eardrum-position microphone of the ear simulator. Because of the simulator's steel-walled earcanal portion, the inventive electronic earplug reduces the sound output by a maximum of approximately 50 dB for 178 SPL input, for the reason described above. The net result is that FIG. 8 differs from the graph in FIG. 7 in two ways: (1) the output SPLs shown in FIG. 7 are 5 dB lower because the data in FIG. 8 are reported directly and not corrected, and (2) FIG. 7 graph illustrates a maximum 35 dB attenuation, which is typical for a three-flange eartip for inputs between 150 and 180 dB SPL.

In FIG. 8, the output vs. input relationship is linear (with a slope of about 1) up to about 117 dB SPL. Then, between input of about 117 dB SPL and about 170 dB SPL, the sound output remains constant at around 122 dB SPL. In other words, as measured in a Zwislocki Coupler ear simulator, the inventive electronic earplug reduces inputs between about 117 dB SPL and about 170 dB SPL to about 122 dB SPL. At an input of about 178 dB SPL, the sound output is about 128 dB SPL, 50 dB of attenuation as described above.

Figure 9:
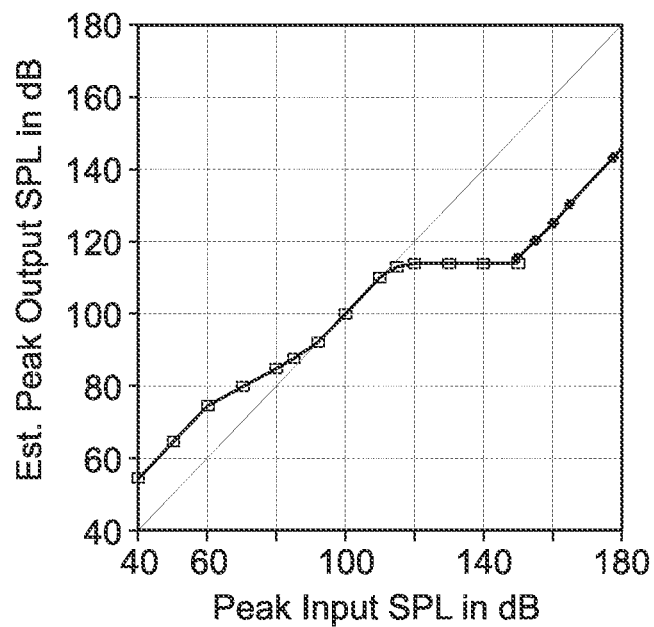
FIG. 9 is a graph depicting peak sound pressure level received at an electronic earplug vs. peak sound pressure level delivered to a user's ear canal for an electronic earplug used in accordance with embodiments of the present technology.

FIG. 9 is a graph depicting peak sound pressure level received at an electronic earplug vs. peak sound pressure level delivered to a user's ear canal for an electronic earplug used in accordance with embodiments of the present technology. The electronic earplug depicted in FIG. 9 provides a 15 dB gain for sounds up to about 60 dB SPL received at the electronic earplug microphone. Between about 60 dB SPL and about 90 dB SPL, the electronic earplug provides a level of gain that decreases linearly from about 15 dB to 0 dB as sound input to the electronic earplug microphone increases. Between about 90 dB SPL and about 115 dB SPL sound is delivered to the user's ear canal via the electronic earplug at the same dB SPL that sound is received at the electronic earplug microphone. For sound input levels between about 115 dB SPL and about 150 dB SPL, sound is delivered to the user's ear canal via the electronic earplug at about 115 dB SPL. For sound input levels above 150 dB SPL, the level of sound in the ear canal is determined by the effective noise isolation provided by the electronic earplug/eartip. Electronic earplugs configured to perform as depicted in FIG. 9 can provide amplification for sound levels up to about 90 dB SPL, sound without gain or attenuation between about 90 dB SPL and about 115 dB SPL, and hearing protection over 115 dB SPL.

Figure 10:
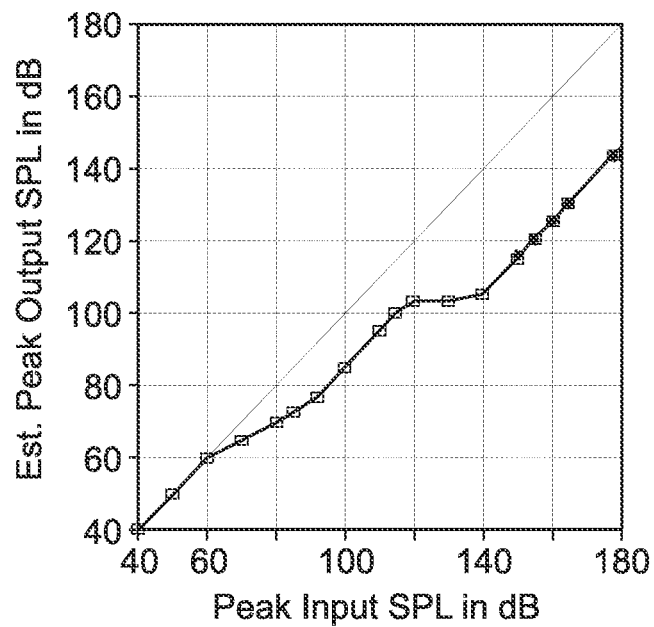
FIG. 10 is a graph depicting peak sound pressure level received at an electronic earplug vs. peak sound pressure level delivered to a user's ear canal for an electronic earplug used in accordance with embodiments of the present technology.

FIG. 10 is a graph depicting peak sound pressure level received at an electronic earplug vs. peak sound pressure level delivered to a user's ear canal for an electronic earplug used in accordance with embodiments of the present technology. Up to about 60 dB SPL, the electronic earplug depicted in FIG. 10 delivers sound to the user's ear canal via the electronic earplug at the same dB SPL that sound is received at the electronic earplug microphone. Between about 60 dB SPL and about 90 dB SPL, the electronic earplug provides a level of attenuation that increases linearly from 0 dB to about 15 dB as sound input to the electronic earplug microphone increases. Between about 90 dB SPL and about 120 dB SPL, the electronic earplug provides about 15 dB of attenuation. For sound input levels between about 120 dB SPL and about 140 dB SPL, sound is delivered to the user's ear canal via the electronic earplug at about 105 dB SPL. For sound input levels above 140 dB SPL, the level of sound in the ear canal is determined by the effective noise isolation provided by the electronic earplug/eartip. Electronic earplugs configured to perform as depicted in FIG. 10 can provide sound without gain or attenuation up to about 60 dB SPL, attenuation for sound levels between about 60 dB SPL and about 120 dB SPL, and blast and extremely intense noise protection over 120 dB SPL.

In certain embodiments, an electronic earplug can include a switch with an on setting configured to perform as indicated in FIG. 7, FIG. 9 or FIG. 10. In certain embodiments, an electronic earplug can include a switch with a first on setting configured to perform as indicated in FIG. 7, and a second on setting configured to perform as indicated in FIG. 9. In certain embodiments, an electronic earplug can include a switch with a first on setting configured to perform as indicated in FIG. 7, and a second on setting configured to perform as indicated in FIG. 10. In certain embodiments, an electronic earplug can include a switch with a first on setting configured to perform as indicated in FIG. 9, and a second on setting configured to perform as indicated in FIG. 10. In certain embodiments, an electronic earplug can include a switch with a first on setting configured to perform as indicated in FIG. 7, a second on setting configured to perform as indicated in FIG. 9, and a third on setting configured to perform as indicated in FIG. 10.

Figure 10A:
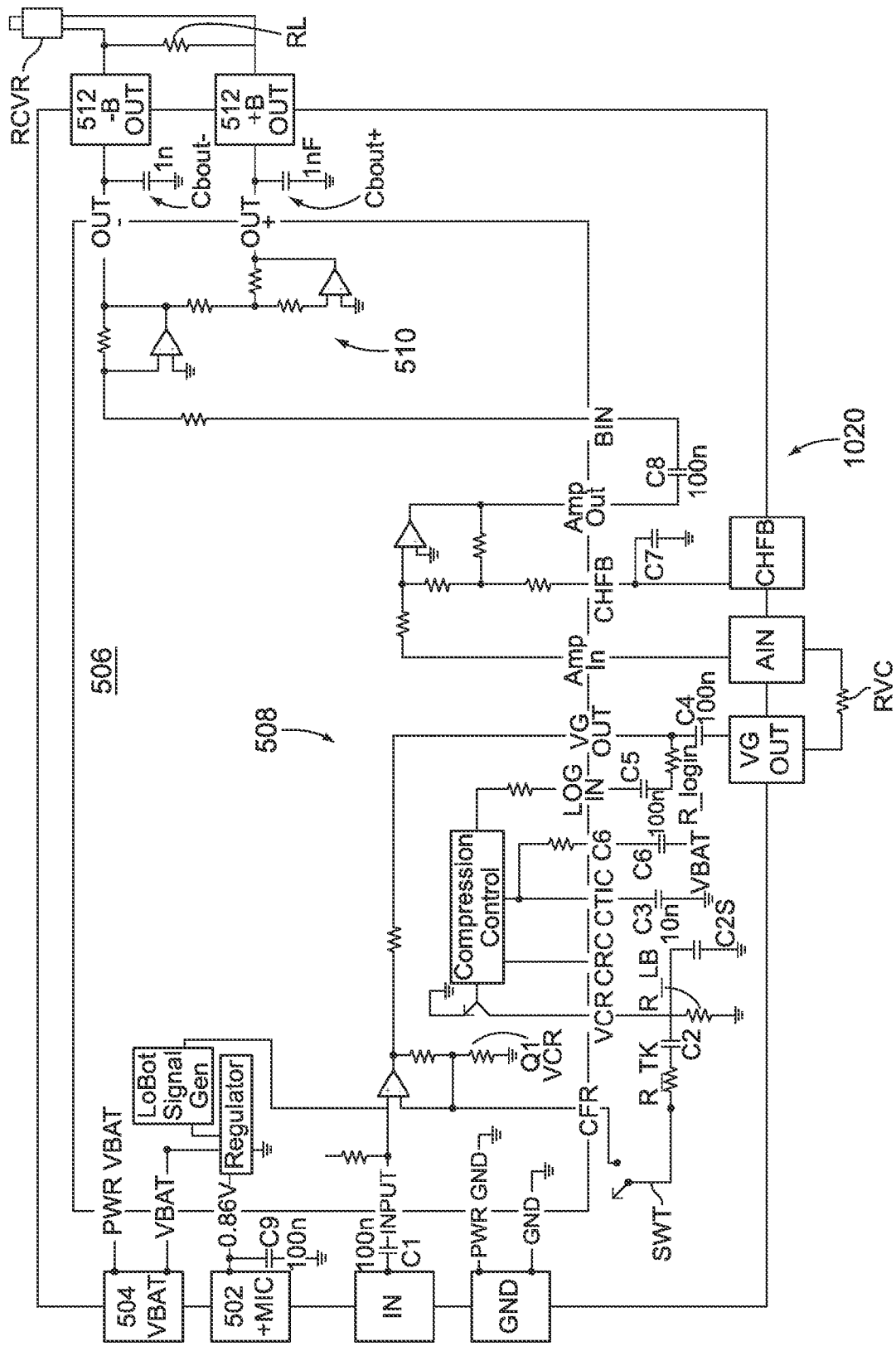
FIG. 10A is a circuit diagram depicting electronic earplug components and circuitry used in accordance with embodiments of the present technology.

In an embodiment, an electronic earplug can include a hybrid circuit configured such that the electronic earplug can be switched between functioning as depicted in FIG. 7 and FIG. 9 by throwing a single pole single throw switch in series with the Threshold Knee controlling portion of the circuit. Such circuitry is depicted in FIG. 10A, which is similar to FIG. 4 of U.S. patent application Ser. No. 12/207,317, by Johnson et al. (published Mar. 11, 2010 as U.S. App. Pub. No. 2010/0061576), which application is incorporated herein by reference in its entirety. Beside the modifications described herein, the circuitry depicted in FIG. 10A would function as the circuitry described in the published application. FIG. 10A is a circuit diagram 1020 depicting electronic earplug components and circuitry, where switch SWT controls the gain for soft sounds below 60 dB SPL. If a fixed value of resistor RVC=115 kOhm is connected into the circuit, then there will be 0 dB gain for sounds between 90 and 115 dB, as described above in connection with FIGS. 7 and 9. With switch SWT in the open circuit position, the characteristic of FIG. 7 is obtained, i.e., 0 dB gain also for sounds below 115 dB. When switch SWT is closed, resistor R_TK has a value of 4.7 kOhms to provide 15 dB of gain for sounds below 60 dB SPL, while leaving 0 dB gain between 90 and 115 dB as shown in FIG. 9 above.

Figure 10B:
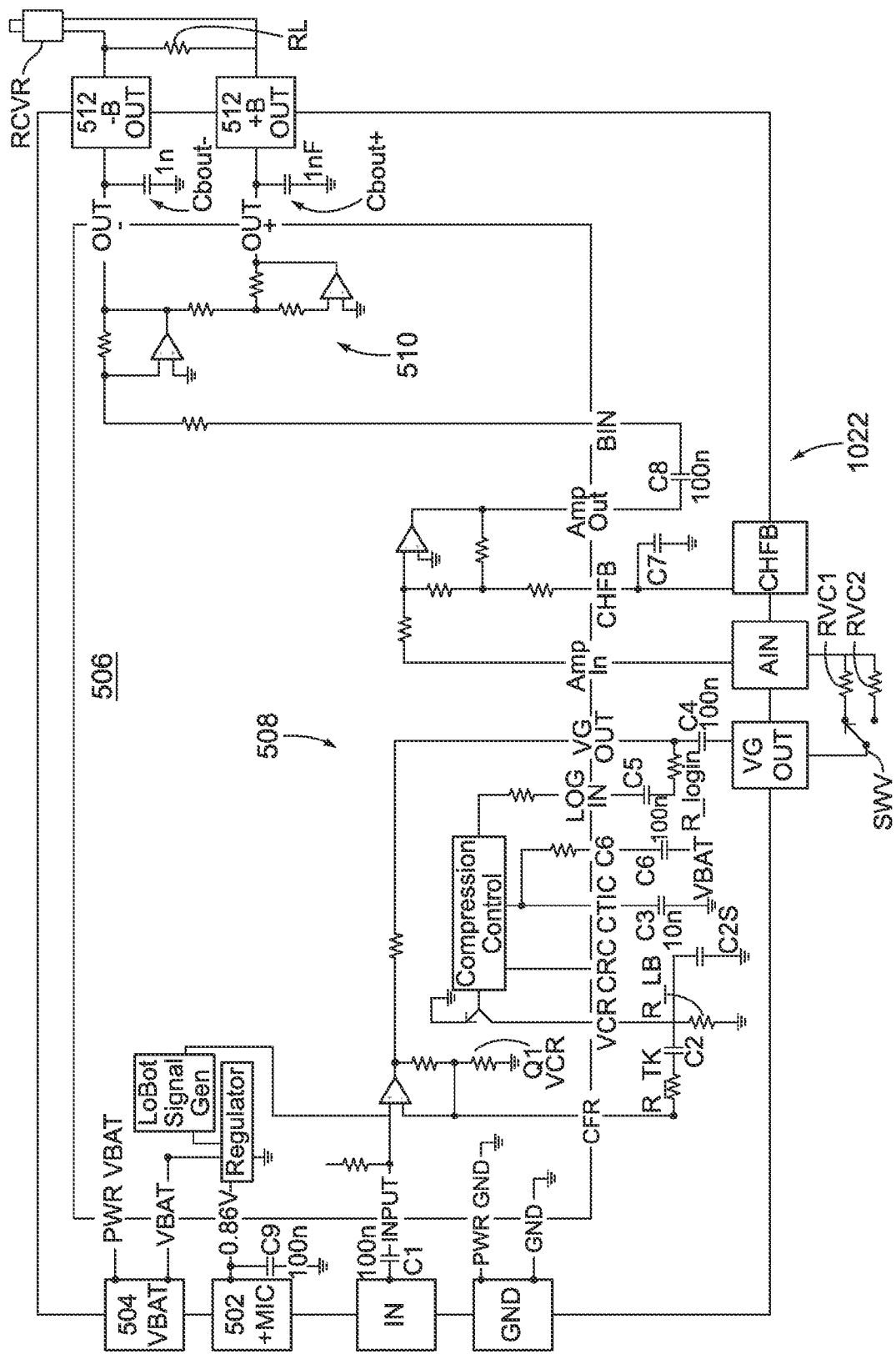
FIG. 10B is a circuit diagram depicting electronic earplug components and circuitry used in accordance with embodiments of the present technology.

In an embodiment, an electronic earplug can include a hybrid circuit configured such that the electronic earplug can be switched between functioning as depicted in FIG. 9 and FIG. 10 by throwing a single pole double throw switch to select two different volume control resistors. Such circuitry is depicted in FIG. 10B, which is similar to FIG. 4 of U.S. patent application Ser. No. 12/207,317, by Johnson et al. (published Mar. 11, 2010 as U.S. App. Pub. No. 2010/0061576), which application is incorporated herein by reference in its entirety.

Beside the modifications described herein, the circuitry depicted in FIG. 10B would function as the circuitry described in the published application. FIG. 10B is a circuit diagram 1022 depicting electronic earplug components and circuitry, where a fixed value of 4.7 kOhm can be connected as resistor R_TK, producing an increase in gain of 15 dB for soft sounds below 60 dB SPL. When switch SWV is connected to resistor RVC1, which may be a 115 kOhm resistor, then the characteristic shown in FIG. 9 is obtained. When switch SWV is connected to resistor RVC2, which may be 634 kOhm resistor, then a gain of 0 dB for soft sounds below 60 dB SPL is obtained, while an attenuation of 15 dB will be obtained for sounds between 60 and 90 dB SPL as shown in FIG. 10. A hearing protection action is thus provided to those who must work around noisy equipment and Humvee-like vehicles.

In certain embodiments, an electronic earplug can be configured to function as depicted in FIG. 9, except that external sound can be attenuated at 105 dB SPL rather than 115 dB SPL. In such embodiments, the electronic earplug can provide a 15 dB gain for sounds up to about 60 dB SPL received at the electronic earplug microphone. Between about 60 dB SPL and about 90 dB SPL, the electronic earplug provides a level of gain that decreases linearly from about 15 dB to 0 dB as sound input to the electronic earplug microphone increases. Between about 90 dB SPL and about 105 dB SPL sound is delivered to the user's ear canal via the electronic earplug at the same dB SPL that sound is received at the electronic earplug microphone. For sound input levels between about 105 dB SPL and about 150 dB SPL, sound is delivered to the user's ear canal via the electronic earplug at about 105 dB SPL. For sound input levels above 150 dB SPL, the level of sound in the ear canal is determined by the effective noise isolation provided by the electronic earplug/eartip. Electronic earplugs configured to perform as described can provide amplification for sound levels up to about 90 dB SPL, sound without gain or attenuation between about 90 dB SPL and about 105 dB SPL, and hearing protection over 105 dB SPL.

This additional attenuation to a maximum of 105 dB SPL output can be obtained in the circuit of FIG. 10A or 10B by adding a single resistor RL across the terminals of the receiver RCVR. It has been found that a value of 150 Ohms will produce the desired output limiting with negligible effect on the circuit function in other regions. To explain, the described circuit has negative feedback around the outputs at 512−BOUT and 512+BOUT, and thus presents a low source impedance as seen by the receiver RCVR. Thus the voltage delivered to the receiver is unaffected by the presence of the resistor until the maximum output current capability of the circuit is reached, at which point clipping occurs such that output is limited 10 dB below the level depicted in FIGS. 7 and 9 (e.g., down to 105 dB SPL). In other words, the value of 150 Ohms causes clipping to occur at roughly 10 dB below normal clipping for the circuit.

In certain embodiments, an electronic earplug can include gain control that is independent of the attenuation control, such that a user can set a preferred gain level for quiet sounds and a preferred attenuation level for loud sounds. For example, one switch can be configured to be manipulated among a plurality of positions in order to manipulate a sound output level increase for the electronic earplug, and a second switch can be configured to be manipulated among a plurality of positions in order to manipulate a sound output level decrease for the electronic earplug.

In certain embodiments, the circuit 106 can include a battery polarity reversing circuit 108 that can detect the polarity of the battery 116 and, if necessary, reverse the polarity. This can allow the battery that powers the electronic earplug to be inserted either way (i.e., such that the negative and positive ends are not required to be situated in a specific orientation), as described, for example in U.S. Pat. No. 5,623,550 issued to Killion et al. on Apr. 22, 1997. This can allow a battery to be replaced quickly and/or in low light situations.

Certain embodiments can include a circuit design that signals when battery power is below a certain point, as described, for example in U.S. Pat. No. 6,704,424 issued to Killion et al. on Mar. 9, 2004, and U.S. Pat. No. 6,320,969 issued to Killion et al. on Nov. 20, 2001.

Electronic earplug 100 also includes a removal string 122 that can be used to retrieve the electronic earplug when it is disposed/inserted in the ear canal. The removal string extends from the exterior facing end of the electronic earplug, and is a stiff element, not a limp string.

Figure 11:
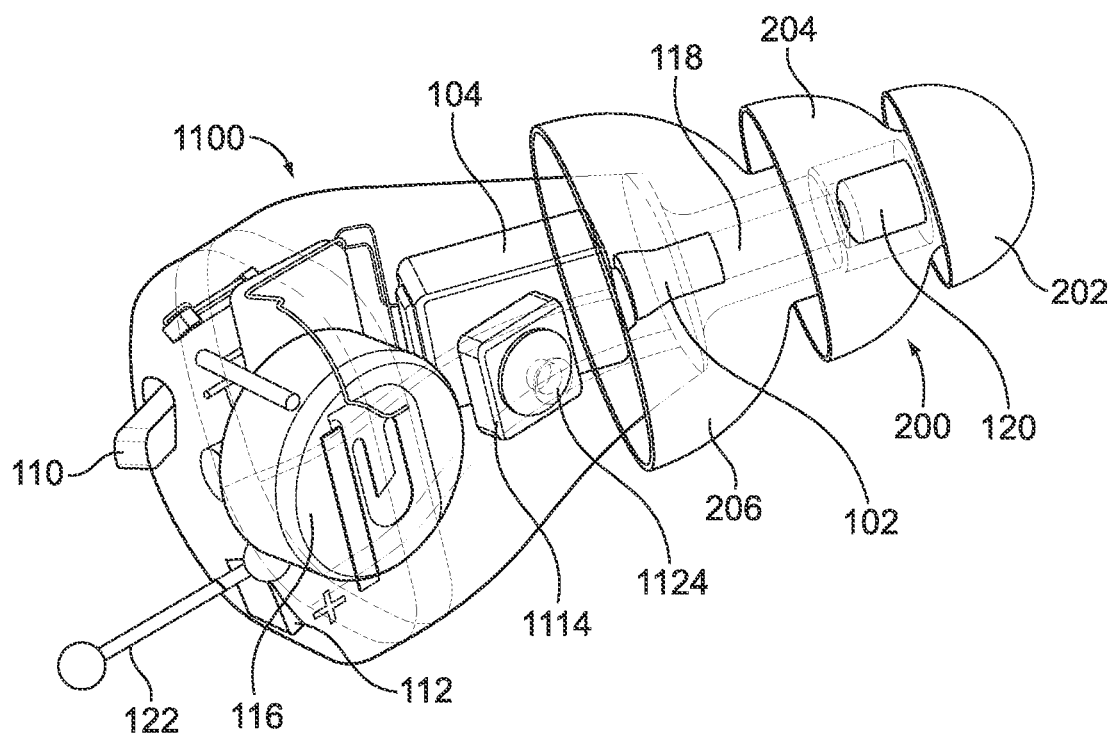
FIG. 11 depicts an electronic earplug used in accordance with embodiments of the present technology.
Figure 12:
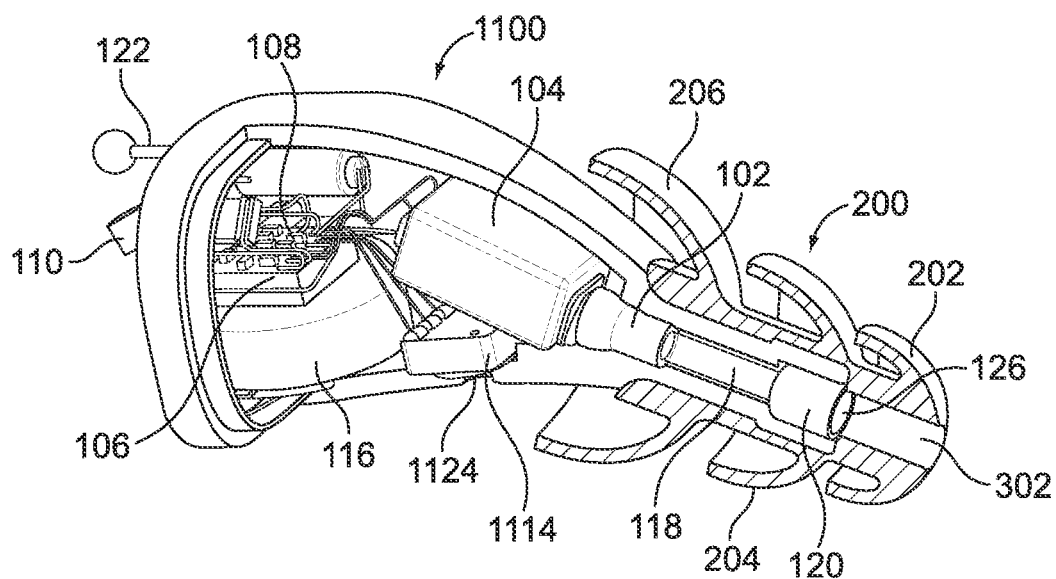
FIG. 12 depicts a cross section of the electronic earplug of FIG. 11.
Figure 13:
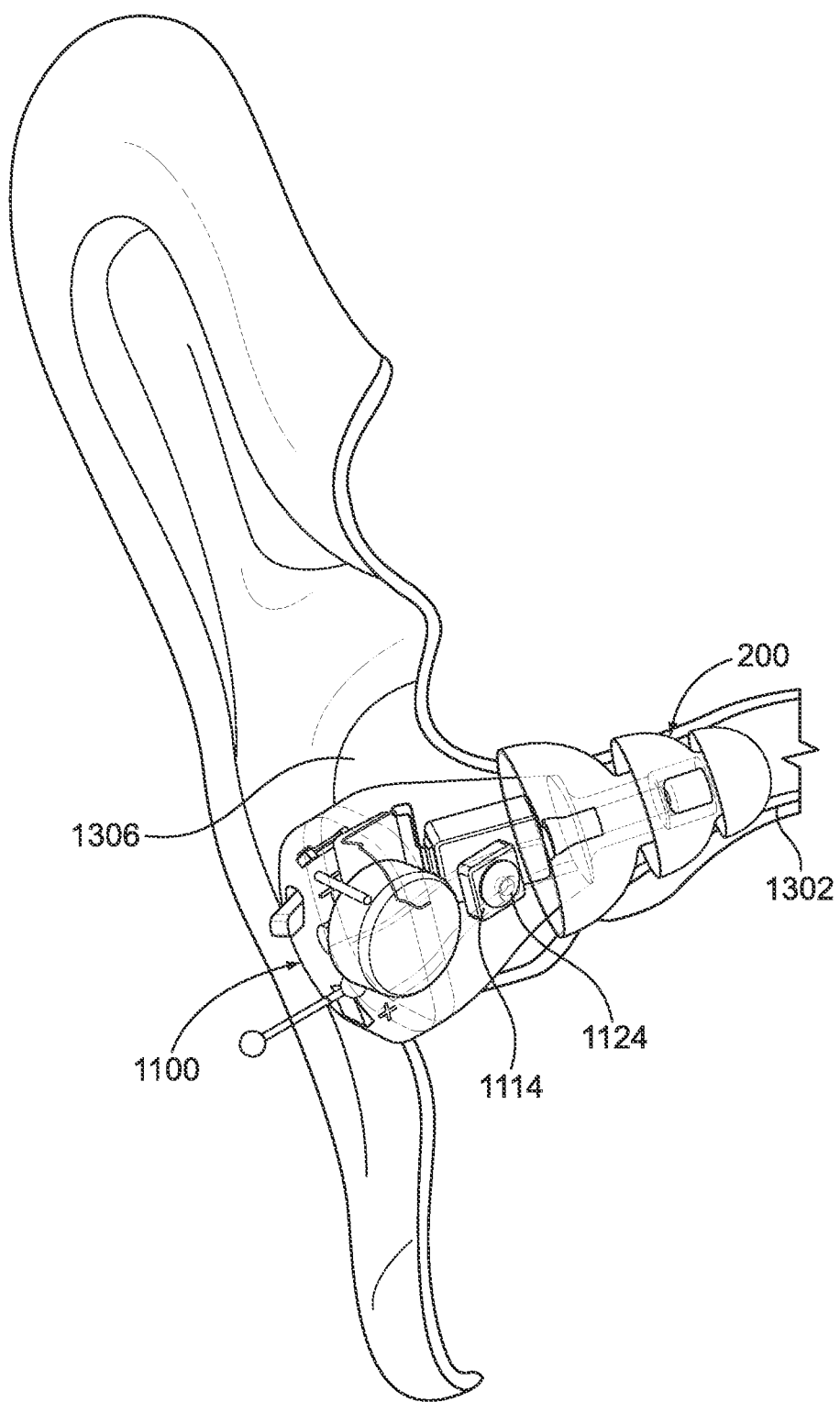
FIG. 13 depicts the electronic earplug of FIG. 11 inserted into a user's ear canal.

FIG. 11 depicts an electronic earplug 1100 used in accordance with embodiments of the present technology. FIG. 12 depicts a cross section of the electronic earplug 1100. FIG. 13 depicts the electronic earplug 1100 inserted into a user's ear canal 1302. The electronic earplug 1100 includes many of the same elements as electronic earplug 100, however, sound inlet 1124 is disposed on a side of the electronic earplug 1100 rather than on the exterior facing end of the electronic earplug. That is, rather than being disposed on a wall of the electronic earplug 1100 that is opposite sound outlet 126, sound inlet 1124 is disposed on a side wall of the electronic earplug 1100 that is not opposite sound outlet 126. Likewise, microphone 1114 is relocated to accommodate the different sound inlet position. This configuration can allow microphone 1114 to be located in or near the ear canal 1302 when the electronic earplug is being worn. Such a microphone location may provide improved situational awareness due to the fact that the microphone is located more deeply into the ear's concha 1306 (depicted in FIG. 13), thereby benefitting from vertical localization cues provided by the concha 1306. As to localization cues provided by the concha, see E. A. G. Shaw, Acoustical Factors Affecting Hearing Aid Performance, Ch. 6: The Acoustics of the External Ear, pp. 109-125, Studebaker and Hochberg, eds, University Park Press, 1978.

Certain electronic earplugs described herein can be fully supported in the ear canal without requiring additional attachment to the user as described, for example, in U.S. Pat. No. RE 38,351 issued to Iseberg et al. on Dec. 16, 2003.

Certain electronic earplugs described herein can be implemented as a one-size-fits-all electronic earplug. Such embodiments can include eartips configured to accommodate the shape of a user's ear canal. For example, the eartips described above (three-flanged eartips (FIGS. 2-4), cylindrical foam eartips (FIG. 5), and mushroom-shaped foam eartips (FIG. 6)) can be used in such embodiments. Such eartips can provide for external noise reduction of up to about 35 dB or greater.

Certain electronic earplugs described herein can be implemented as a custom-fit earmold. Such embodiments can provide for external noise reduction of up to about 35 dB or greater.

Certain electronic earplugs described herein can provide a low cost (e.g., $80-$210) electronic earplug.

Certain electronic earplugs described herein can provide high fidelity sound with a unity gain of 0 dB at levels up to about 105 or 115 dB SPL, such that the sound received in a user's ear canal is substantially the same as that received by the electronic earplug.

Certain electronic earplugs described herein can provide a user with natural localization cues. This can be provided, for example, by the location of the microphone in the concha.

Certain electronic earplugs described herein can provide a user with hearing protection for sounds over about 105 or 115 dB SPL without compromising situational awareness.

Certain electronic earplugs described herein can provide a user with hearing protection for sounds that last up to about 1-3 milliseconds.

Certain electronic earplugs described herein can provide a user with a removable acoustic damper/wax filter that can be easily replaced, for example, when wax build-up clogs the damper.

In certain embodiments, the electronic earplug can be coupled with a two-way wireless communication device such as a one-way or two-way radio, a cell phone or a PDA, for example. Such embodiments can include a microphone configured to receive spoken cues from the wearer of the electronic earplug. The microphone can be a noise canceling microphone configured to reduce noise that is not an audible cue from the wearer of the electronic earplug. The audible cues received at the microphone can be transmitted from the communication device. Also, transmissions received at the communication device can be conveyed to the wearer via the electronic earplug. Such embodiments can allow two-way communication in combination with the previously described sound attenuation and/or amplification provided by the electronic earplug.

Figure 14:
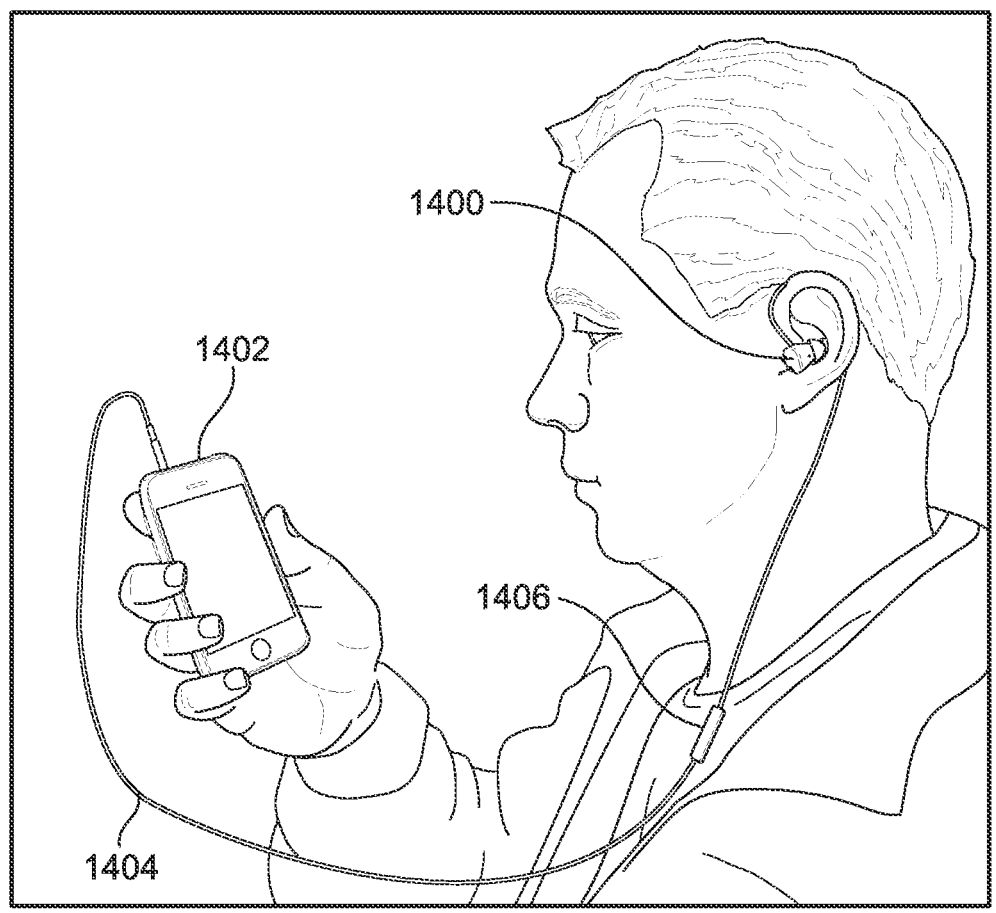
FIG. 14 depicts an embodiment where an electronic earplug is in electrical communication with a two-way communication device using a wire.

FIG. 14 depicts an embodiment where an electronic earplug 1400 is in electrical communication with a two-way communication device 1402 using a wire 1404. A microphone 1406 configured to receive audible cues from the wearer of the electronic earplug 1400 is disposed on the wire 1404. The audible cues received at the microphone 1406 can be transmitted from the communication device 1402. Also, transmissions received at the communication device 1402 can be conveyed to the wearer via the electronic earplug 1400. Such an embodiment can allow received transmissions to be communicated to one ear, while the other ear is protected using an electronic earplug that is not connected to the two-way communication device 1402.

Figure 15:
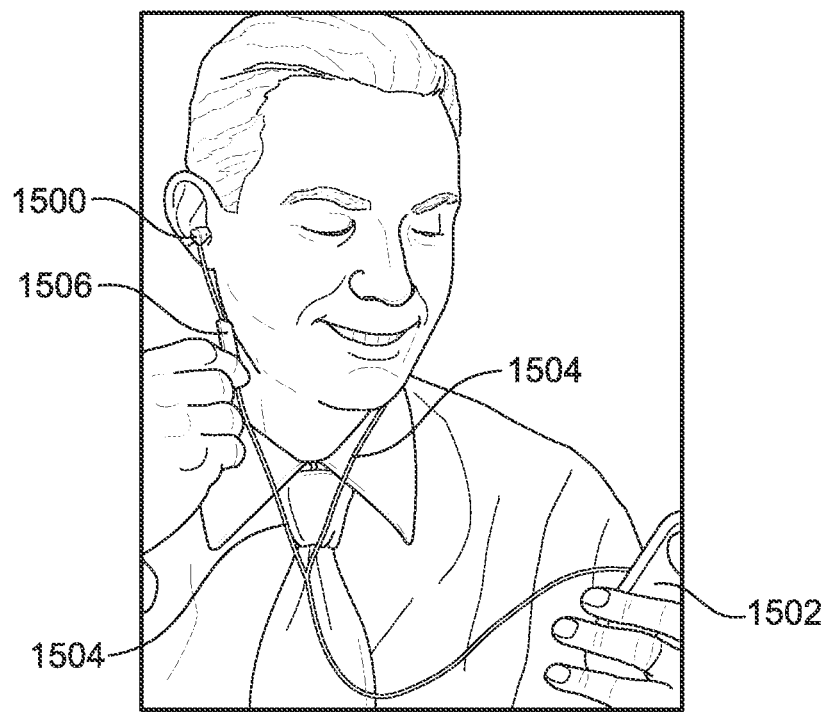
FIG. 15 depicts an embodiment where two electronic earplugs are in electrical communication with a two-way communication device using wires.
Figure 16:
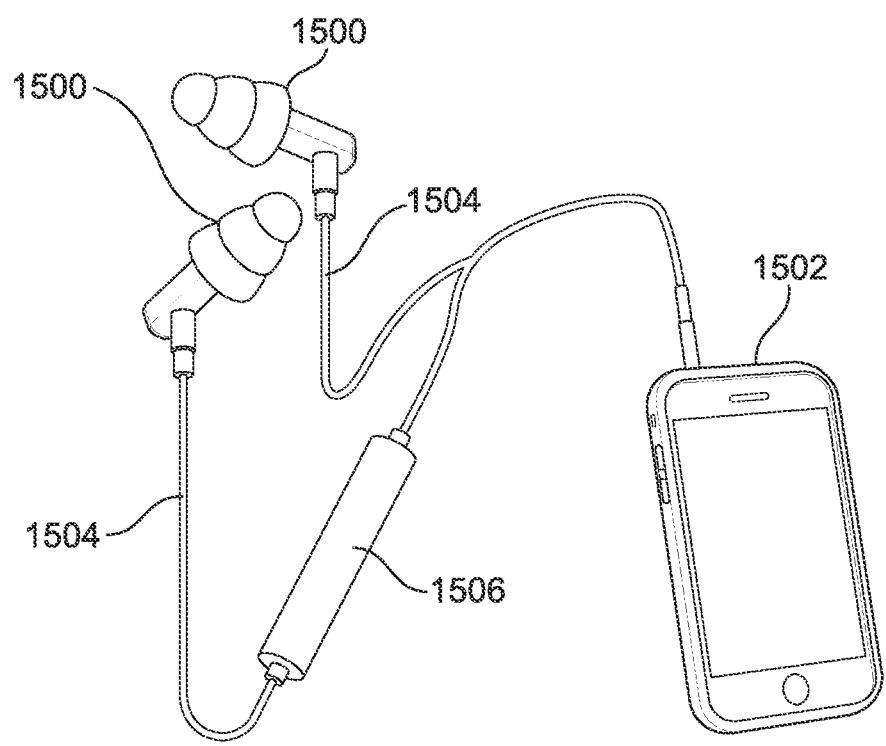
FIG. 16 depicts an embodiment where two electronic earplugs are in electrical communication with a two-way communication device using wires.

FIGS. 15-16 depict an embodiment where two electronic earplugs 1500 are in electrical communication with a two-way communication device 1502 using wires 1504. A microphone 1506 configured to receive audible cues from the wearer of the electronic earplugs 1500 is disposed on one of the wires 1504. The audible cues received at the microphone 1506 can be transmitted from the communication device 1502. Also, transmissions received at the communication device 1502 can be conveyed to the wearer via the electronic earplugs 1500. Such an embodiment can allow received transmissions to be communicated to both ears.

Figure 17:
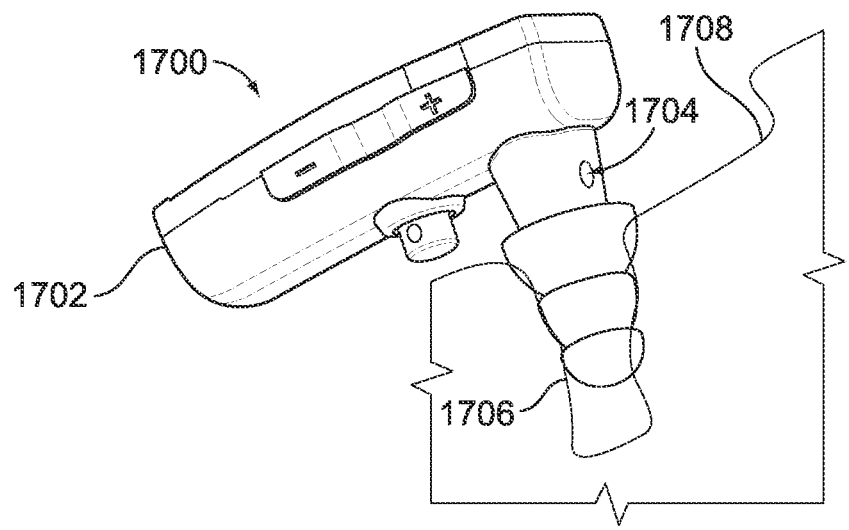
FIG. 17 depicts an embodiment where an electronic earplug is attached to a headset that is in wireless communication with a two-way communication device.

FIG. 17 depicts an embodiment where an electronic earplug as described herein is implemented with a headset 1700 in wireless communication with a two-way communication device. A directional noise-cancelling microphone 1702 configured to receive spoken cues from the wearer is disposed on an end of the headset. The audible cues received at the microphone 1702 can be transmitted from the headset 1700 to the communication device, and can then be transmitted from the communication device. Also, transmissions received at the communication device can be conveyed to the wearer via the headset 1700. Such an embodiment can allow received transmissions to be communicated to one ear, while the other ear is protected using an electronic earplug that is not connected to the two-way communication device.

Headset 1700 also includes an omnidirectional ("omni") microphone 1704 disposed on the housing such that the microphone 1704 will be located in or near the user's ear canal 1706 when the electronic earplug is being worn. It has been found that such a microphone location can provide improved situational awareness. This improvement may be due to the microphone being provided more deeply into the ear's concha 1708, thereby benefitting from vertical localization cues provided by the concha 1708. As to localization cues provided by the concha, see E. A. G. Shaw, Acoustical Factors Affecting Hearing Aid Performance, Ch. 6: The Acoustics of the External Ear, pp. 109-125, Studebaker and Hochberg, eds, University Park Press, 1978.

Figure 18:
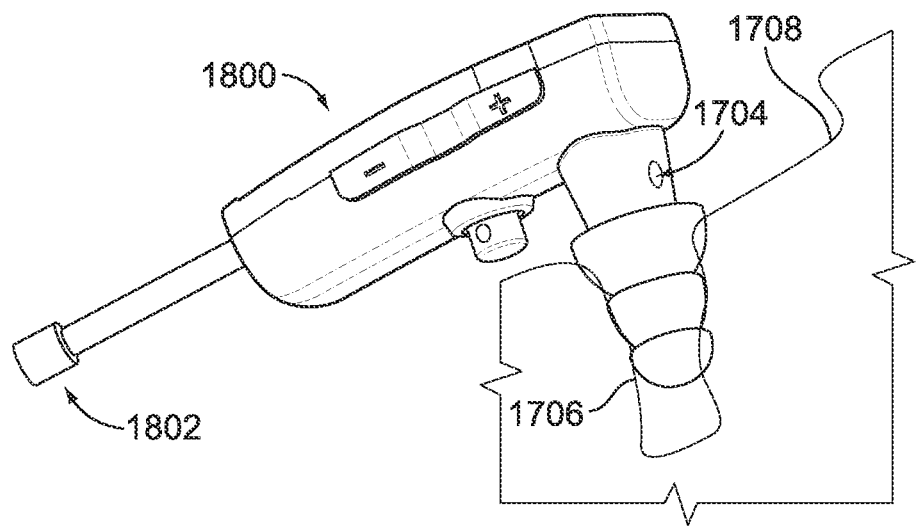
FIG. 18 depicts an embodiment where an electronic earplug is attached to a headset that is in wireless communication with a two-way communication device.

FIG. 18 depicts an embodiment where an electronic earplug as described herein is implemented with a headset 1800 in wireless communication with a two-way communication device. The headset 1800 functions like headset 1700, however, a directional noise-cancelling microphone 1802 configured to receive audible cues from the wearer of the electronic earplug is disposed on a boom extending from the headset rather than on an end of the headset.

Embodiments such as those described in connection with FIGS. 17-18, for example, can be useful in situations where a soldier is using a communication device to receive commands, and also needs to hear local situational cues such as gunfire or local commands.

Some situational awareness is possible through the noise-cancelling boom microphone, but the boom microphone is highly directional which provides an unnatural sound pickup. In certain embodiments, a switch can be used to switch between the boom microphone and the omni (situational) microphone. In other embodiments that include a boom microphone and an omni (situational) microphone, no switch is needed to achieve desired performance. A switchless option can also be implemented in embodiments that employ a receive coil for receiving radio transmissions, such embodiments being described in further detail in connection with FIGS. 22-22C.

Figure 19A:
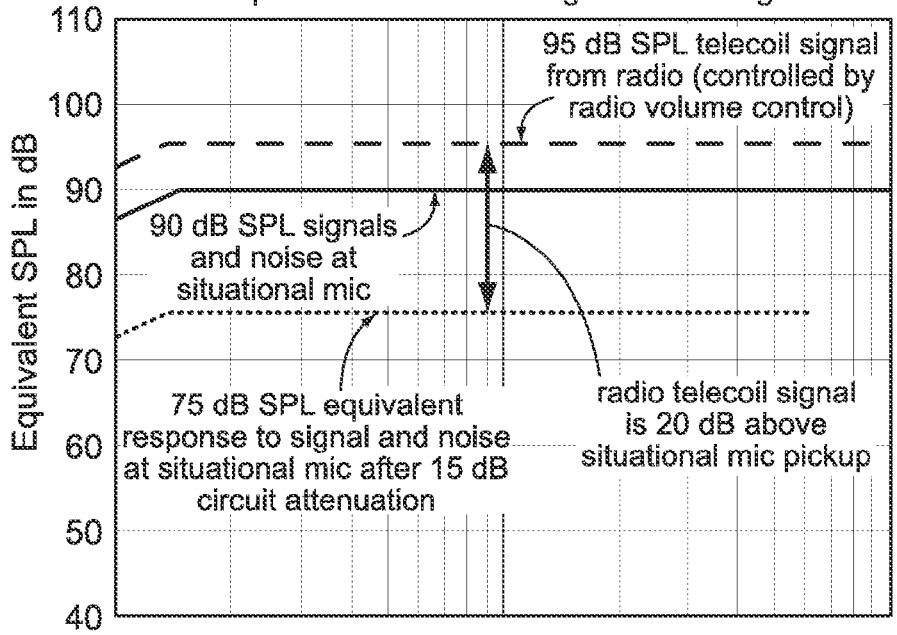
FIG. 19A is a graph depicting characteristics of sound delivered to a user of a headset with a boom (directional) microphone, a situational (omni-directional) microphone, and a receive coil configured to receive radio signals.
Figure 19B:
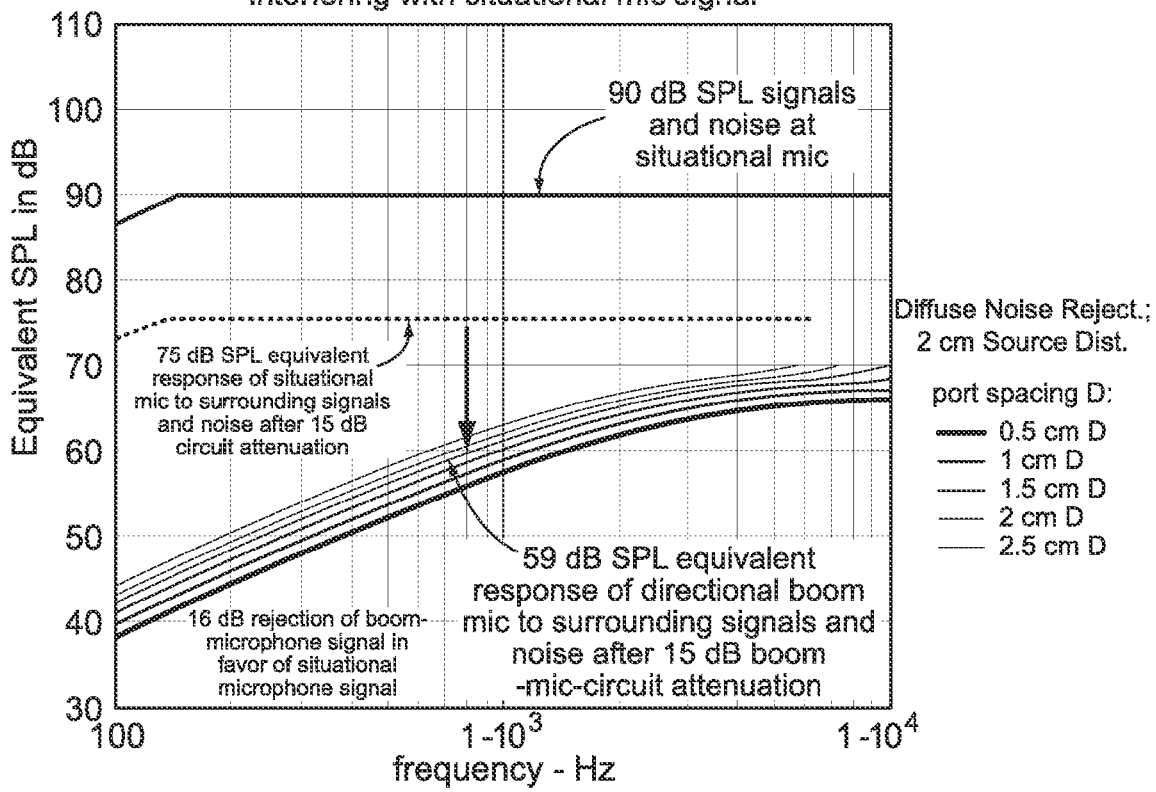
FIG. 19B is a graph depicting characteristics of sound delivered to a user of a headset with a boom (directional) microphone and a situational (omni-directional) microphone.
Figure 19C:
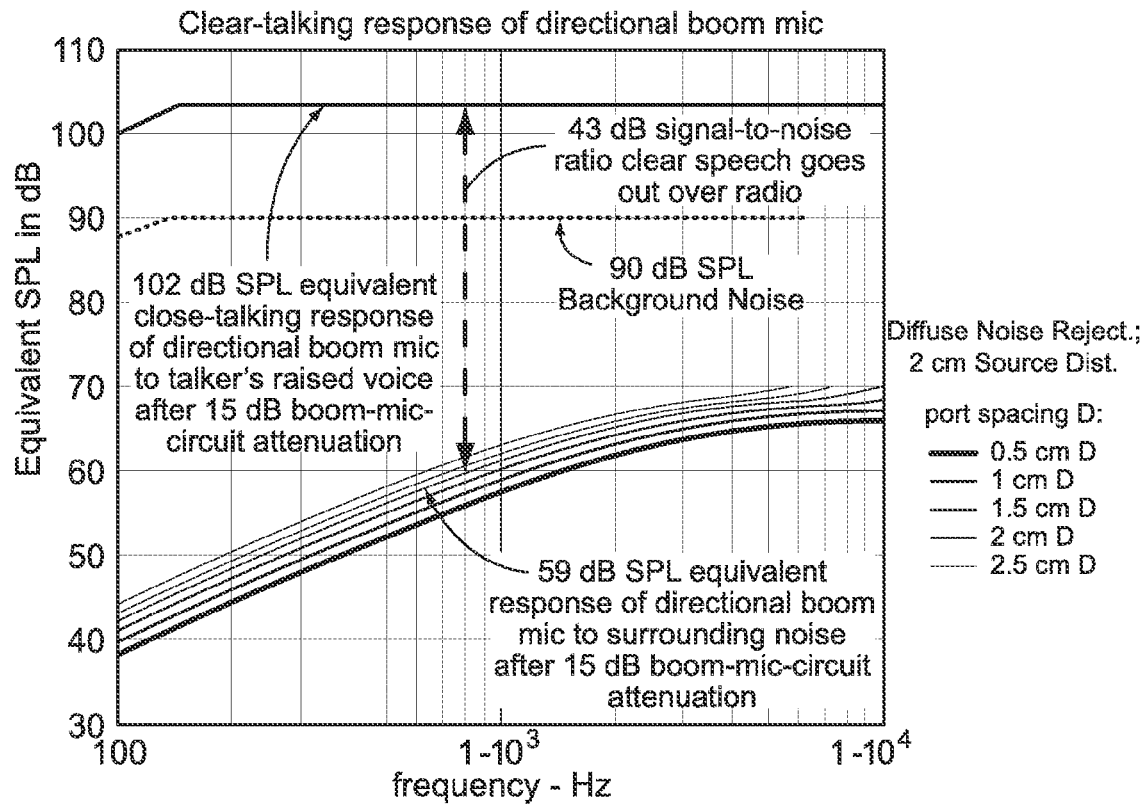
FIG. 19C is a graph depicting the noise cancellation characteristics of a directional microphone vs. an omni-directional microphone.

FIGS. 19A, 19B, and 19C illustrate favorable cooperation of the three signals (which are summed into the amplifier input) without requiring any mechanical or electrical switching, and while maintaining good signal-to-noise ratio in each case. The three signals being: (1) the radio-reception signal received by a receive coil, (2) the wearer-talker signal received by the boom (directional) microphone, and (3) the ambient background signals from the situational (omni-directional) microphone.

As depicted in FIG. 19A, the situational (omni-directional) microphone can be left on without interfering with the reception of radio signals via the receive coil by a user because the radio signals are provided to the user at 95 dB SPL (controlled by radio volume) while sounds received at the situational (omni-directional) microphone are provided to the user at 90 dB SPL. The boom (directional) microphone can also be left on without interfering with a user's reception of radio signals from the receive coil because sounds received at the boom (directional) microphone are only provided to the user at 75 dB SPL.

As depicted in FIG. 19B, the boom (directional) microphone can also be left on without interfering with a user's reception of situational cues from the situational (omni-directional) microphone because ambient sound picked up by the noise-cancelling boom (directional) microphone will be approximately 15 dB lower than the ambient sound picked up by the situational (omni-directional) microphone.

Figure 20:
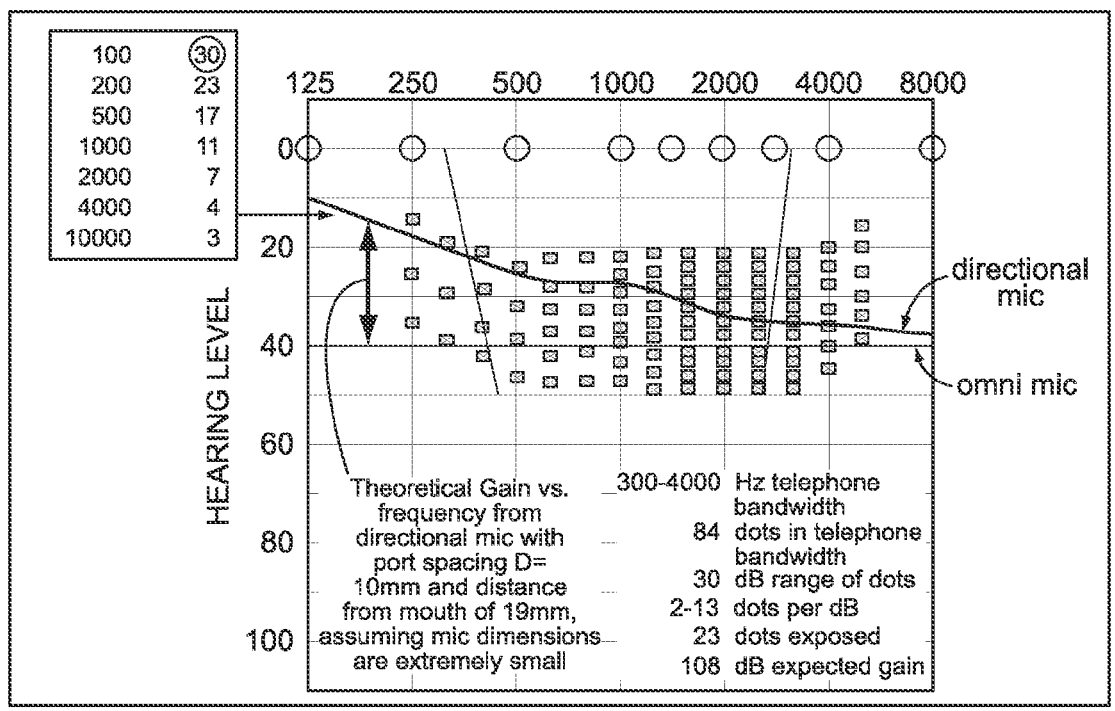
FIG. 20 is a graph depicting theoretical gain vs. frequency from a directional microphone vs. an omni-directional microphone.

On the other hand, when the user talks, the sound of his voice will be picked up some 15 dB greater by the boom (directional) microphone compared to the situational (omnidirectional) microphone due to proximity to the user's mouth. See, for example, FIGS. 19C and 20, which provide graphical representations of the voice pick up improvement achieved by the noise-cancelling boom (directional) microphone. Thus, when the user speaks, the output from the situational (omnidirectional) microphone should be relatively negligible. By balancing the outputs of the two microphones and then summing them into the amplifier input, a switchless solution can be obtained. Further, as depicted in FIG. 19C, certain embodiments can provide a clear signal from the noise-cancelling boom (directional) microphone up to at least about 100 dB SPL of ambient background noise. This is consistent with experiments where listeners receive signals from the Etymotic etyBLU Bluetooth headset (which uses the same boom microphone) while the headset is being used in a test environment with 100 dB SPL of ambient background noise. In response to such tests, some listeners that receive signals from the headset say they "almost didn't hear any noise," while the user that speaks into the headset often reports that he or she cannot even hear themselves talk due to the ambient background noise level.

Figure 21:
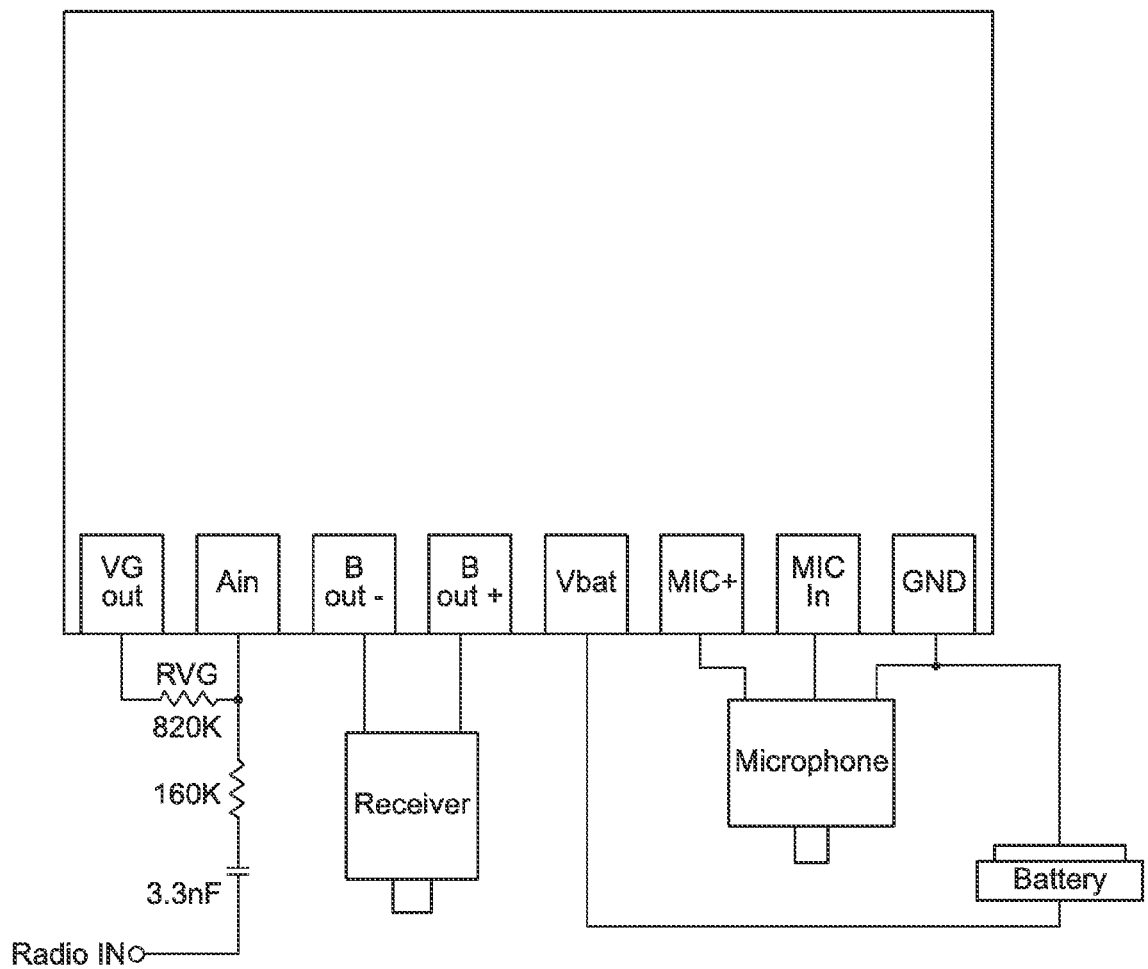
FIG. 21 depicts a circuit diagram for a hybrid amplification circuit used in embodiments where an electronic earplug is coupled with a two-way wireless communication device.

FIG. 21 depicts a circuit diagram for a hybrid amplification circuit used in embodiments where an electronic earplug is coupled with a two-way wireless communication device. The circuit can allow signals received at the electronic earplug from the communication device to be converted into sound and delivered to a wearer of the electronic earplug.

With most devices, as the background noise increases, the user must stop and turn up the volume control on the radio. The result may be a radio volume so loud that hearing becomes distorted and the user cannot understand, as has often been reported. Commercially available hearing protection devices combine a shaped earplug with a small processor/control unit to provide active noise cancellation and the ability to interface with a communications device. These devices provide an improved ability to block loud constant or impulse noises while allowing the ability to participate in a conversation or talk on a radio, but issues remain with comfort, situational awareness, speech intelligibility, localization, and identification. These systems range in cost from $1,200-$1,500 per unit when purchased in large quantities.

In embodiments of the present technology, as the background noise increases above 60 dB, the gain can go down until at about 90 dB the signal from the microphone has been turned down 15 dB, while the signal from the radio is unaffected. In many cases, therefore, the user need not touch either volume control because the automatic wide-dynamic-range compression of the electronic earplug hybrid circuit will have made the adjustment for the soldier. In other words, the electronic earplug circuit can be configured such that up to about 60 dB, ambient noise received at the electronic earplug microphone is increased by about 15 dB. As ambient noise received at the electronic earplug microphone increases above 60 dB, the gain can be decreased, for example, linearly at a rate of 0.5 dB gain decrease for every 1 dB increase in ambient noise received at the electronic earplug microphone, until ambient noise received at the electronic earplug microphone reaches about 90 dB, and the signal from the microphone has been turned down 15 dB. Over the same range, the sound level of signals received at the electronic earplug from a two-way communication device can be held constant. Such embodiments can allow ambient noise levels to be automatically manipulated, while the sound level from signals received from a two-way communication device remains constant.

In certain embodiments, to avoid wires while allowing radio communication (for example, from a military radio or a cellphone), magnetic coupling can be used, for example, as described in the following U.S. patents: U.S. Pat. No. 7,099,486 issued to Julstrom et al. on Aug. 29, 2006; U.S. Pat. No. 7,206,426 issued to Julstrom et al. on Apr. 17, 2007; and U.S. Pat. No. 7,522,740 issued to Julstrom et al. on Apr. 21, 2009.

Figure 22:
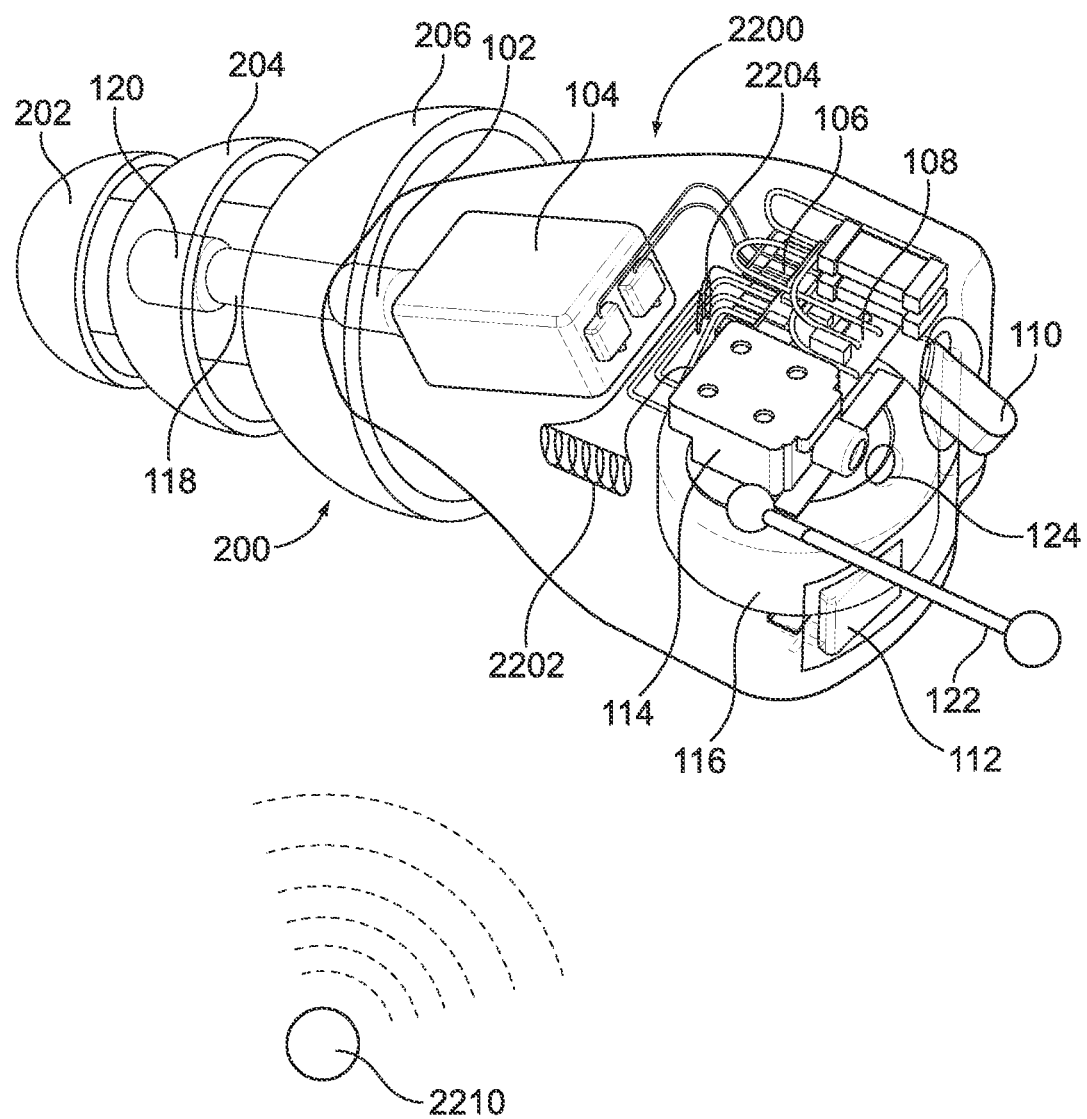
FIG. 22 depicts an embodiment where an electronic earplug is in communication with a communication device using a receive coil.

As depicted in FIG. 22, electronic earplug 2200 can include many of the elements of electronic earplug 100, and can also include receive coil 2202 and switch 2204. Receive coil 2202 can be configured to be magnetically coupled to a remote transmit coil 2210 that is operably connected to a radio and/or telephone, for example, when the remote transmit coil 2210 provides an adequate field level. Receive coil 2202 can include a long axis that can be aligned to be substantially parallel with a long axis of sound channel 118 such that receive coil 2202 will be similarly oriented when electronic earplug 2200 is rotated in a user's ear canal. Such a configuration can allow receive coil 2202 to magnetically couple to remote transmit coil 2210 in a similar fashion regardless of the rotational positioning of electronic earplug 2200 in a user's ear canal. Switch 2204 can be configured to switch the input from the electronic earplug microphone 114 to receive coil 2202 once the receive coil 2202 senses an adequate field level. In certain embodiments, switch can be configured, for example, as described in U.S. Pat. No. 6,694,034 issued to Julstrom et al. on Feb. 17, 2004. Communications can then be received at electronic earplug receive coil 2202 from remote transmit coil 2210.

For use with telephones, the switch level can be set fairly low, such as at a field strength of about 40 mA/m (equivalent to the field in a 1 turn coil of 1 meter diameter with 40 mA alternating current flowing through the receive coil) or less, for example. However, it has been found that background noise levels near fluorescent lights can be as high as 30 mA/m, and in military environments even higher levels may exist. By use of drive coils (as described in the aforementioned patents, for example), however, fields at 2000 to 5000 mA/m can be produced by remote transmit coil 2210. Thus, setting the switch threshold at about 500 mA/m or greater can prevent unintended operation from background magnetic noise.

In another embodiment, receive coil 2202 can be wired in series with the electronic earplug microphone 114 without using switch 2204. In such embodiments, a field level of 1000 mA/m at electronic earplug receive coil 2202 can be made equivalent in voltage to electronic earplug microphone 114 receiving 80 dB SPL (by bridging receive coil 2202 with a low-value resistor, for example). In this case, normal background magnetic noise (about 20-30 dB re 1 mA/m) is quiet enough to be masked by normal room noise of 45 dB, and will not trigger unintended operation from background magnetic noise.

Used in connection with the electronic earplugs described herein, the receive coil option can allow situational awareness to continue while maintaining radio contact. At a 15-25 dB attenuation by an electronic earplug, for example, an outside sound level of 95 dB SPL would be dropped to 70-80 dB SPL. Assuming a field strength of 3200 mA/m could be obtained at the receive coil input, by turning the radio up to maximum volume, the radio level would be 90 dB SPL, which would permit a good signal-to-noise ratio, while still allowing a user to keep track of his surroundings.

Figure 22A:
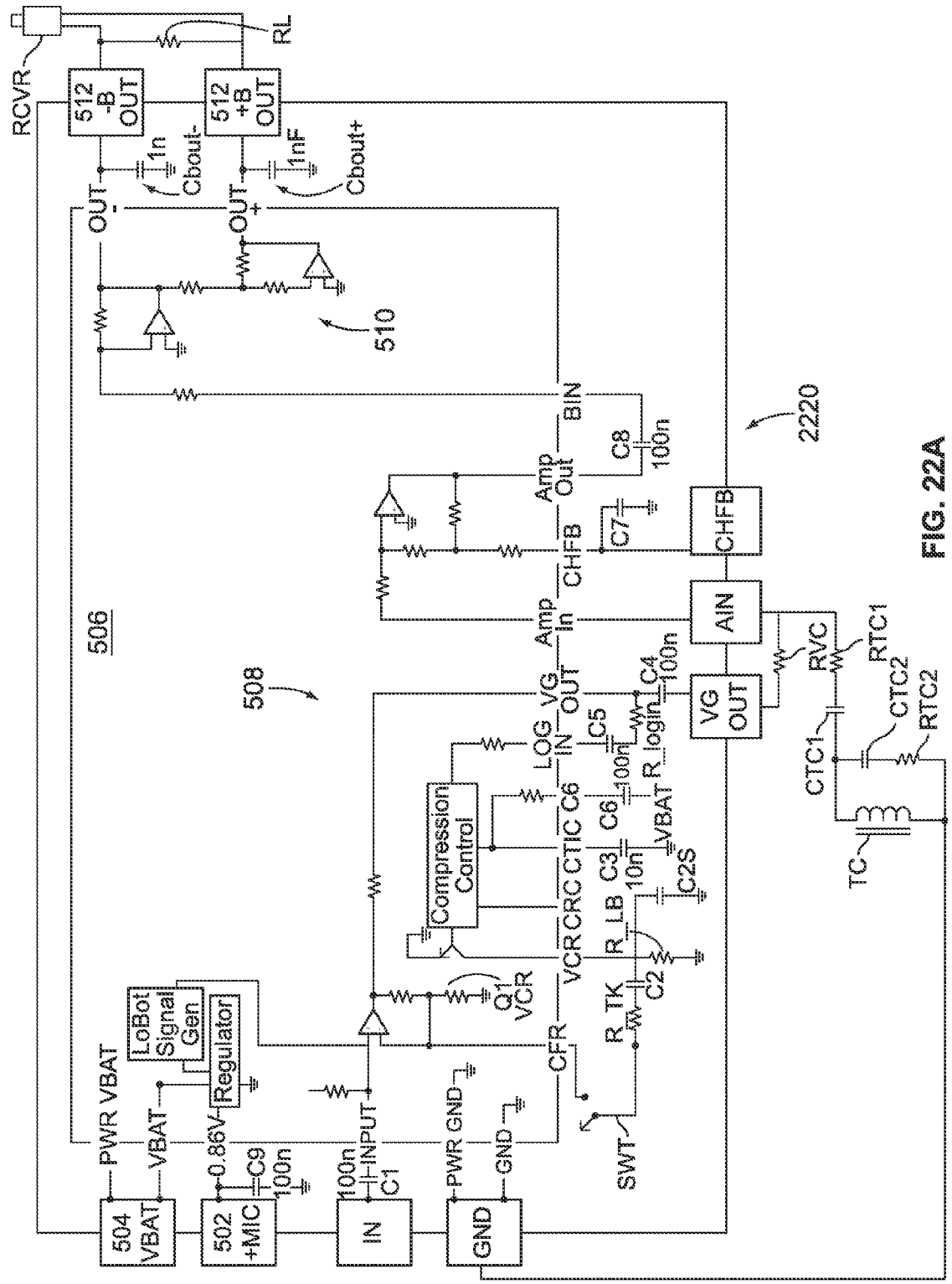
FIG. 22A is a circuit diagram depicting electronic earplug components and circuitry used in an embodiment of an electronic earplug that is in communication with a communication device using a receive coil.

FIG. 22A is a circuit diagram 2220 depicting electronic earplug components and circuitry used in an embodiment of an electronic earplug that is in communication with a communication device using a receive coil. In FIG. 22A, receive coil TC is wired into the hybrid circuit depicted in FIG. 10A. That is, receive coil TC is connected in series with resistor RTC1 and capacitor CTC1 and fed into the input of the output amplifier, bypassing the amplification circuit that provides the change in gain between 60 and 90 dB SPL inputs (a gain change that is illustrated in FIG. 9). An improved frequency response can be obtained with the addition of the R-C filter comprised of resistor RTC2 and capacitor CTC2. In certain embodiments, receive coil TC can be Tibbits coil #Y44-xx-JFR.

One problem encountered was that of obtaining sufficient magnetic field to permit use of receive coil TC, which is rather small in size. It has been found that a sufficient magnetic field (for example, of more than 10 A/m) can be obtained using a properly designed and configured earloop in combination with an audio output level found in Army radios. Thus the volume control on the radio can provide a range of useful levels from soft up to nearly 95 dB SPL. One advantage of wiring which bypasses the gain-changing circuit is that the output level in the ear is dependent only on the setting of the volume control on the radio, and is independent of the user settings or choice of electronic earplug (characteristics illustrated in FIGS. 7, 9, and 10). In certain embodiments, the wearer can adjust the radio volume control for the best relationship between radio volume level and the level of outside sounds.

In certain embodiments, an earloop as described above can comprise a circular ring including 20 turns of #40 wire (less than 0.1 oz) on one or both ears. In a preferred embodiment, the earloop is centered over the ear such that the receive coil inside the electronic earplug is centered within the earloop. FIG. 22B depicts an embodiment where earloop 2304 is maintained relative to a user's ear using headband 2302. In such embodiments, earloop 2304 can be attached to or embedded in headband 2302. In other embodiments, such an earloop can be maintained relative to a user's ear(s) in another manner, such as by attaching or embedding in a helmet, hat, or other article placed on a user's head.

Similarly, it has been found that a properly configured headband loop can be used in place of an earloop. FIG. 22C depicts an embodiment where headband loop 2308 is maintained relative to a user's ears using headband 2306. In such embodiments, headband loop 2308 can be attached to or embedded in headband 2306. In other embodiments, such a headband loop can be maintained relative to a user's ear(s) in another manner, such as by attaching or embedding in a helmet, hat, or other article placed on a user's head. In certain embodiments, a headband loop as described above can comprise 13 turns of #29 wire, and can produce in excess of 10 A/m at the receive coil oriented as shown in FIG. 22 when driven by a typical Army radio. It has also been found that a 2 oz neckloop (worn around the neck like a necklace) including 84 turns of #29 wire can produce at least 5 A/m at the receive coil, and even greater field strengths can be obtained with heavier coils.

Figure 22D:
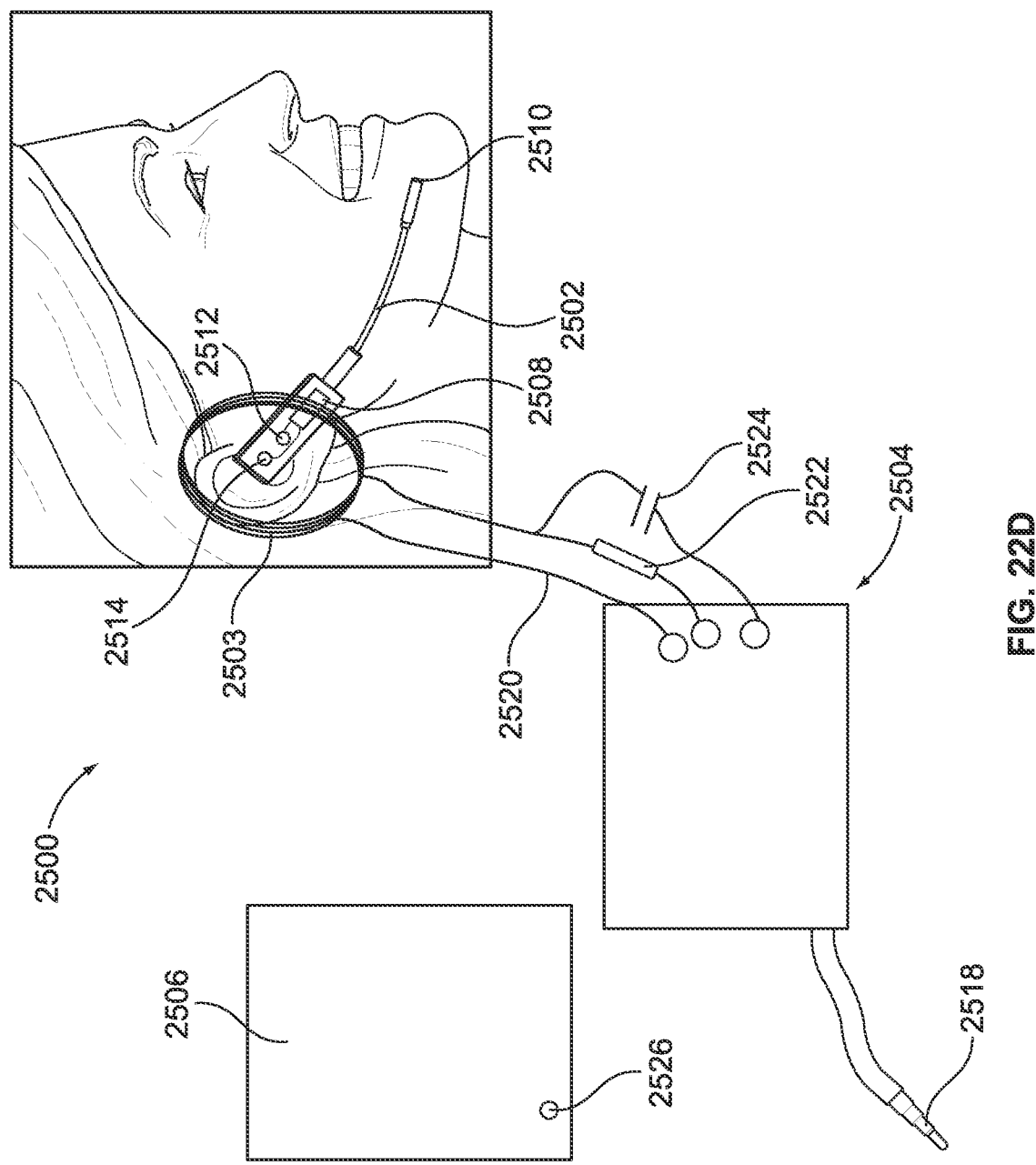
FIG. 22D depicts a system for wireless communication between a wireless headset including a transmit coil and a receive coil and radio interface loops used in accordance with embodiments of the present technology.

In certain embodiments, a wireless headset that receives audio signals inductively using a receive coil and generates audio signal transmissions using a transmit coil can be provided in combination with electronic earplugs described herein. FIG. 22D depicts a two-way communication system 2500 that includes a wireless headset 2502, radio interface loop 2503, radio interface module 2504, and two-way radio 2506. Radio interface loop 2503 can be maintained in proximity to wireless headset 2502 such that audio signals can be inductively communicated between radio interface loop 2503 and transmit and receive coils disposed within wireless headset 2502. In certain embodiments, radio interface loop 2503 can comprise earloops, a headband and/or a neckloop. In the case of earloops, a radio interface loop 2503 can be positioned relative to one ear of a user or both ears of the user. In certain embodiments, radio interface loop 2503 can be maintained relative to a wireless headset by attaching or embedding in a helmet, hat, headband or other article placed on a user's head.

Headset 2502 includes circuitry 2508 configured to convert signals received inductively at receive coil 2514 into sound that can be communicated to a user's ear canal. Circuitry 2508 is also configured to convert sound received at boom microphone 2510 into signal transmissions that are generated using transmit coil 2512. In certain embodiments, receive coil 2514 can inductively receive baseband audio signals, and transmit coil 2512 can generate pulse-duration-modulated ("PDM") signals or frequency modulated ("FM") signals in order to transmit sound received at a boom microphone 2510.

In certain embodiments, receive coil 2514 and transmit coil 2512 are both situated in headset 2502 such that the long axis of each coil extends substantially parallel to a sound duct configured to deliver sound to a user's ear canal, and such that the long axis of each coil extends substantially perpendicular to a side of a user's head when headset 2502 is being worn by the user with the eartip inserted into the user's ear canal. In certain embodiments, transmit coil 2512 and receive coil 2514 can be offset such that receive coil 2514 is provided in a field orientation null of transmit coil 2512. For example, in certain embodiments, receive coil 2514 and transmit coil 2512 can be situated in headset 2502 such that the long axis of receive coil 2514 extends substantially parallel to the long axis of transmit coil 2514, and the coils 2512, 2514 can be shifted relative to each other along their long axes a sufficient distance such that receive coil 2514 is provided in a field orientation null of transmit coil 2512. In certain embodiments, such a sufficient relative shifting can place one end of transmit coil 2512 across from the approximate midpoint of the long axis dimension of receive coil 2514.

Radio interface loop 2503 is configured to transmit signals that can be received inductively using receive coil 2514. Radio interface loop 2503 is also configured to inductively receive signals generated by transmit coil 2512. Radio interface loop 2503 is in wired communication with radio interface module 2504, which is operably connected to two-way radio 2506, for example using audio plug 2518 and audio jack 2526 configured to receive audio plug 2518. Two-way radio 2506 can be a short range radio, such as a walkie-talkie, for example.

Signals received at two-way radio 2506 can be communicated to radio interface module 2504, conditioned using radio interface module 2504, transmitted from radio interface loop 2503, inductively received at receive coil 2514, conditioned using circuitry 2508, and provided as sound to a user's ear canal. Conversely, sound received at boom microphone 2510 can be conditioned using circuitry 2508, transmitted from transmit coil 2512, inductively received at radio interface loop 2503, demodulated and conditioned using radio interface module 2504, communicated to two-way radio 2506, and transmitted using two-way radio 2506.

Radio interface module 2504 includes circuitry configured to demodulate audio signals generated by transmit coil 2512 and inductively received at radio interface loop 2503. Radio interface module 2504 also includes circuitry configured to filter signals received at and sent from radio interface loop 2503. The circuitry includes high pass filter 2524 that filters audio signals received at radio interface loop 2503 from transmit coil 2512. High pass filter 2524 is configured to prevent baseband audio signals from interfering with demodulation of audio signals generated by transmit coil 2512. The circuitry also includes low-pass choke 2522 that filters audio signals that will be sent from radio interface loop 2503 and received at receive coil 2514. Low-pass choke 2522 is configured to prevent the low-impedance of radio earphone output from shorting out audio signals generated by transmit coil 2512.

In an embodiment where transmit coil 2512 generates PDM signals, circuitry 2508 can include a class D amplifier, such as those described in U.S. Pat. No. 4,592,087 issued to Killion in 1986 and/or U.S. Pat. No. 4,689,819 issued to Killion in 1987, for example, in order to generate the PDM signal. The circuitry of radio interface module 2504 can demodulate the PDM signal using an r-c filter, for example. In certain embodiments, transmit coil 2512 is a low impedance coil that generates a 120 kHz PDM signal and has a self-resonance of, for example, 500 kHz. The 120 kHz PDM signal is picked up by radio interface loop 2503 and then separated from the baseband audio signals transmitted from radio interface loop 2503 using a high-pass filter at about 20 kHz, for example. The 120 kHz PDM signal is then demodulated with an r-c filter back to audio to deliver the sound received at boom microphone 2510 to two-way radio 2506 for transmission to others. In certain embodiments, the total current required by components of the headset 2502, for example, to power: an amplifier used to provide situational awareness in the headset 2502, the boom microphone, and the Class D amplifier, can be less than about 600 uA, permitting more than two months operation on a single 675 battery cell.

In an embodiment where transmit coil 2512 generates FM signals, circuitry 2508 can include an FM modulator such as that described in U.S. Pat. No. 4,592,087 issued to Killion in 1986 and a transmission system as described in U.S. Pat. No. 6,694,034 issued to Julstrom et al. in 2004, for example, in order to generate the FM signal. In certain embodiments, an FM transmitter such as those shown and described in FIGS. 22E and/or 22F can be used to generate the FM signal. The circuitry of radio interface module 2504 can filter and demodulate the FM signals, for example. In certain embodiments, transmit coil 2512 is a low impedance coil that generates a 100 kHz center frequency FM signal and has a self-resonance of, for example, 500 kHz. The 100 kHz FM signal is picked up by radio interface loop 2503 and then separated from the baseband audio signals transmitted from radio interface loop 2503 using a high-pass filter that passes the 100 kHz FM signal substantially unattenuated, but provides significant attenuation to baseband audio frequencies, for example. The 100 kHz FM signal is then demodulated back to audio to deliver the sound received at boom microphone 2510 to two-way radio 2506 for transmission to others. FIG. 22G is a schematic diagram depicting circuitry for a radio interface module and radio interface loops that can be used in accordance with an embodiment of the present technology. In certain embodiments, the total current required by components of the headset 2502, for example, to power: an amplifier used to provide situational awareness in the headset 2502, the boom microphone, and the FM transmitter, can be less than about 600 uA, permitting more than two months operation on a single 675 battery cell.

Figure 22E:
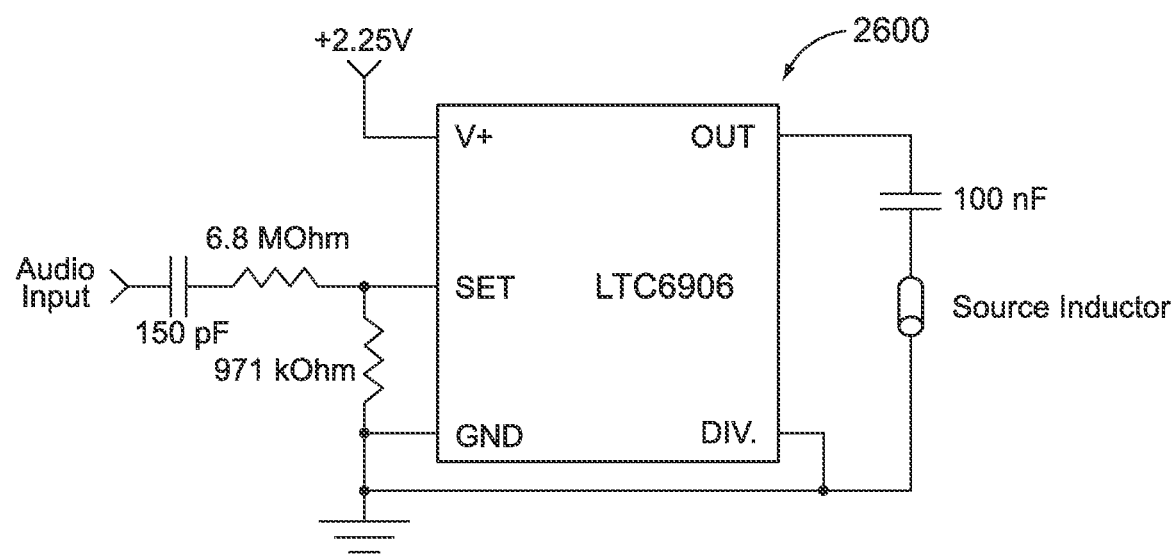
FIG. 22E is a schematic diagram depicting an FM transmitter that can be used in accordance with embodiments of the present technology to generate an FM signal using a transmit coil.

FIG. 22E is a schematic diagram depicting an FM transmitter 2600 that can be used in accordance with embodiments of the present technology to generate an FM signal using transmit coil 2512. The schematic depicts the Linear Technology LTC6906. As shown, a 1 Vpeak, 2 Vpeak-to-peak audio input signal will result in a frequency deviation of +/−22 kHz from a center frequency of 103 kHz (which, for an audio frequency modulation bandwidth of 3 kHz, places the significant modulation sidebands within the frequency range of 78 kHz to 128 kHz). The output can directly drive a small source inductor transmit coil, such as the 1.7 mH source inductor described in connection with FIG. 22H, to a peak-to-peak square-wave drive approaching the 2.25 volt supply voltage. Supply current for this portion of the circuitry should be about 60 uA average, including 10 uA for the integrated circuit operating current and 50 uA for power loss in the integrated circuit output stage and the inductor. To operate from a single, non-Lithium-based power cell of typically 1.2 to 1.5 V, a low-power voltage step-up circuit can be used.

Figure 22F:
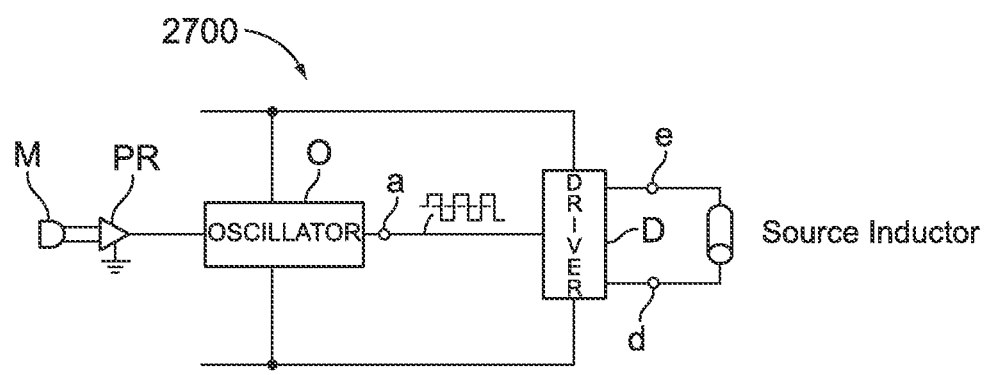
FIG. 22F is a schematic diagram depicting an FM transmitter that can be used in accordance with embodiments of the present technology to generate an FM signal using a transmit coil.
Figure 22G:
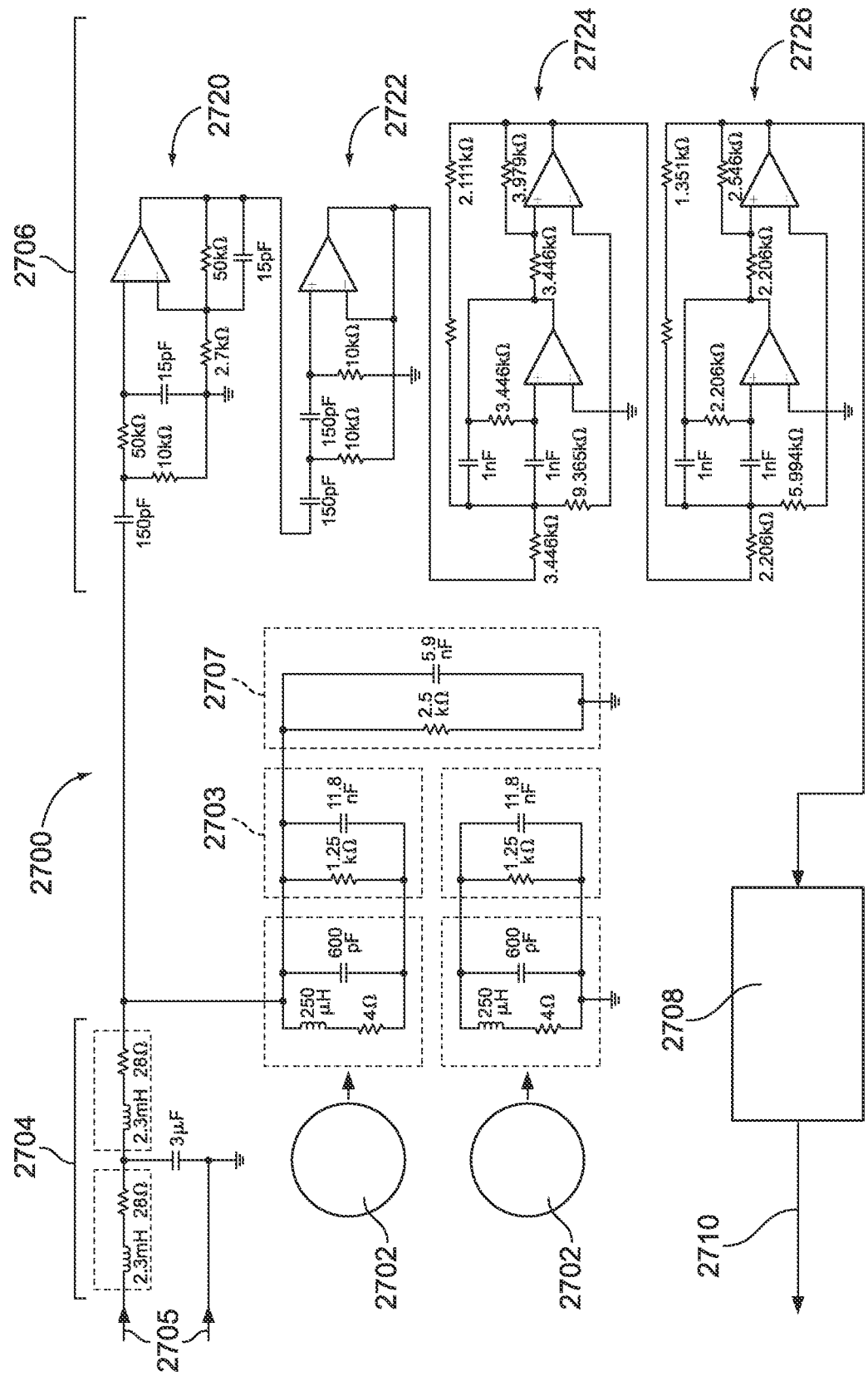
FIG. 22G is a schematic diagram depicting circuitry for a radio interface module and radio interface loops used in accordance with an embodiment of the present technology.

FIG. 22F is a schematic diagram depicting another FM transmitter 2700 that can be used in accordance with embodiments of the present technology to generate an FM signal using transmit coil 2512. In the schematic, the oscillator drives an integrator to produce a triangle waveform that, when modified by an audio input signal, can produce the proper signal information for the low voltage H-bridge output amplifier to produce a frequency-modulated square-wave output, according the teachings of U.S. Pat. No. 4,592,087 to Killion.

FIG. 22G is a schematic diagram depicting circuitry 2700 for a radio interface module and radio interface loops used in accordance with an embodiment of the present technology. The schematic depicts radio interface loops 2702 (e.g., one for each ear), low pass choke 2704, filtering circuitry 2706, and FM demodulator 2708.

As depicted in FIG. 22G, an audio signal can be received at 2705 from a two-way radio, for example, to be transmitted from radio interface loops 2702. Prior to reaching radio interface loops 2702, the audio signal can be passed through low-pass choke 2704 such that high frequency signals above the baseband range of about 300 Hz to about 3 kHz are filtered. In certain embodiments, filtering signals with a frequency above the baseband range can prevent shorting out of audio signals generated by the transmit coil of a headset that are to be inductively received using radio interface loops 2702. The remaining audio signals are transmitted from radio interface loops 2702 such that they can be received inductively at a receive coil in a wireless headset.

As also depicted in FIG. 22G, radio interface loops 2702 can inductively receive audio signals generated by a transmit coil in a wireless headset. The audio signals can be generated based on sound received at a boom microphone of the wireless headset. In the depicted embodiment, the audio signals comprise FM signals. In other embodiments, the audio signals can be PDM signals, for example.

In certain embodiments, radio interface loops 2702 can be configured to exhibit resonance when inductively receiving signals with a frequency of about 100 kHz and can exhibit a Q value of 5. Circuitry indicated by either 2703 or 2707 can provide for the desired resonant frequency and Q and can be located at the radio interface loops 2702 and/or at a radio interface module. For example, in certain embodiments, circuitry 2703 is located at radio interface loops 2702 and can provide for the desired resonant frequency and Q. For example, in certain embodiments, circuitry 2707 is located further from radio interface loops 2702, such as at a radio interface module, for example, and can provide for the desired resonant frequency and Q.

In certain embodiments, each radio interface loop 2702 can be 8 centimeters in diameter and can comprise about 40 turns of #29 insulated wire, and can exhibit 4 Ohms/coil or 8 Ohms in series. In certain embodiments, the radio interface loops 2702 can be provided with an additional 56 Ohms resistance in series, for example, by resistance within low-pass choke 2704, then providing a maximum field strength of +30 dB (A/m) within the central region of radio interface loop 2702 from a 4 Vrms maximum radio output.

Audio signals inductively received at radio interface loops 2702 are directed to filtering circuitry 2706, which can be part of a radio interface module. In certain embodiments, filtering circuitry 2706 can include a series of filters configured to prevent baseband audio signals transmitted from radio interface loops 2702 from interfering with demodulation of audio signals generated by a transmit coil of a headset.

As depicted in FIG. 22G, filtering circuitry 2706 includes in series: a broad bandpass filter 2720, a second order high pass filter 2722, a second order bandpass filter 2724 and another second order bandpass filter 2726. In certain embodiments, broad bandpass filter 2720 can be configured to filter signals with a frequency outside of the range of about 85 kHz to about 210 kHz, and provide gain within its pass-band. In certain embodiments, second order high pass filter 2722 can be configured to filter signals with a frequency below about 106 kHz and exhibit a Q value of about 0.5. In certain embodiments, a second order bandpass filter 2724 can be configured to filter signals with a frequency outside of about 80 kHz and exhibit a Q value of about 15 and a gain of about ×10 at 80 kHz. In certain embodiments, second order bandpass filter 2726 can be configured to filter signals with a frequency outside of about 125 kHz and exhibit a Q value of about 15 and a gain of about ×10 at 125 kHz.

In certain embodiments, filtering circuitry 2706 in combination with radio interface loops 2702 with a resonant frequency of about 100 k Hz can provide a sharply tuned receive band from about 78 kHz to about 128 kHz, allowing frequency deviation of about +/−22 kHz (plus 3 kHz bandwidth for the baseband spectrum) from a center frequency of 103 kHz, while eliminating interference from other magnetic or radiated sources.

After passing through filtering circuitry 2706, the remaining audio signals are passed to FM demodulator 2708 where the signals are demodulated into audio that can be input to a radio, such as a two-way radio, for example, for transmission to a remote radio two-way radio, for example.

Figure 22H:
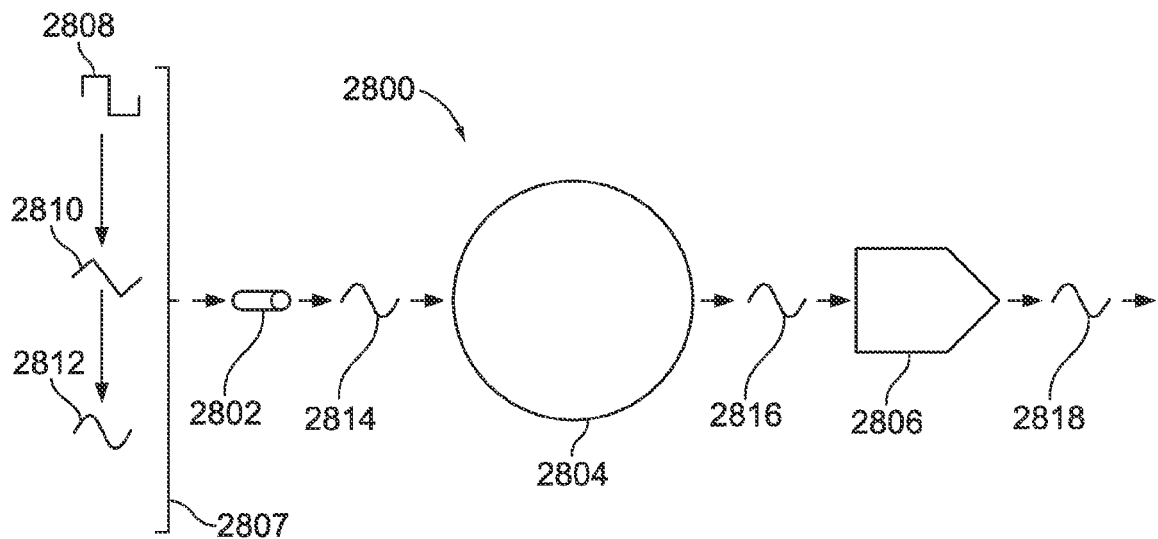
FIG. 22H depicts a system for wireless communication between a wireless headset including a transmit coil and radio interface loops in communication with filtering circuitry used in accordance with an embodiment of the present technology.

FIG. 22H depicts a system 2800 for wireless communication between a wireless headset including a transmit coil 2802 and radio interface loops 2804 in communication with a filtering circuitry 2806 used in accordance with an embodiment of the present technology. The transmit coil 2802 comprises a source inductor that can be used to generate a signal that can be inductively received by radio interface loop 2804. In certain embodiments, the transmit coil can include a ferrite core of 1.6 mm in diameter by 6.6 mm in length and can include a coil winding with 475 turns, which provides for an inductance of 1.7 mH. The radio interface loop 2804 can inductively receive the signal generated by the transmit coil 2802. In certain embodiments, the radio interface loop 2804 can comprise 40 turns of #29 wire, be 8 cm in diameter and can provide for 250 uH per loop when used in series with a second radio interface loop 2804, each loop provided in proximity to an ear of a user. The radio filtering circuitry 2806 can be operably connected to radio interface loop 2804 and can be provided as part of a radio interface module, for example.

In operation, at 2807, when sound is received at a boom microphone of a wireless headset, a 1 Vpeak square wave drive 2808 can be provided to transmit coil 2802, thereby providing 1.47 mApeak of inductor current 2810 to transmit coil 2802 and 1.2 mApeak fundamental frequency current 2812 to transmit coil 2802. At 2814, the transmit coil 2802 will generate a modulated signal that provides an H-field at radio interface loop 2804 of about 55 mA/m peak, 39 mA/m rms and −28 dB (A/m). At 2816, radio interface loop 2804 inductively receives the audio signal such that about 8.7 mVpeak is induced in radio interface loop 2804, which can be magnified to 43 mVpeak by a resonant loop circuit Q=5, in the case of an FM transmission system. At 2818, filtering circuitry 2806 filters and/or applies gain to the audio signal such that a 435 mVpeak filtered signal can be sent to a demodulator. In certain embodiments, the demodulator can include a zero-crossing detector with hysteresis feeding a phase-locked loop, for example. Once demodulated, the signal can be communicated to a two-way radio for transmissions to other two-way radios, for example.

Figure 23:
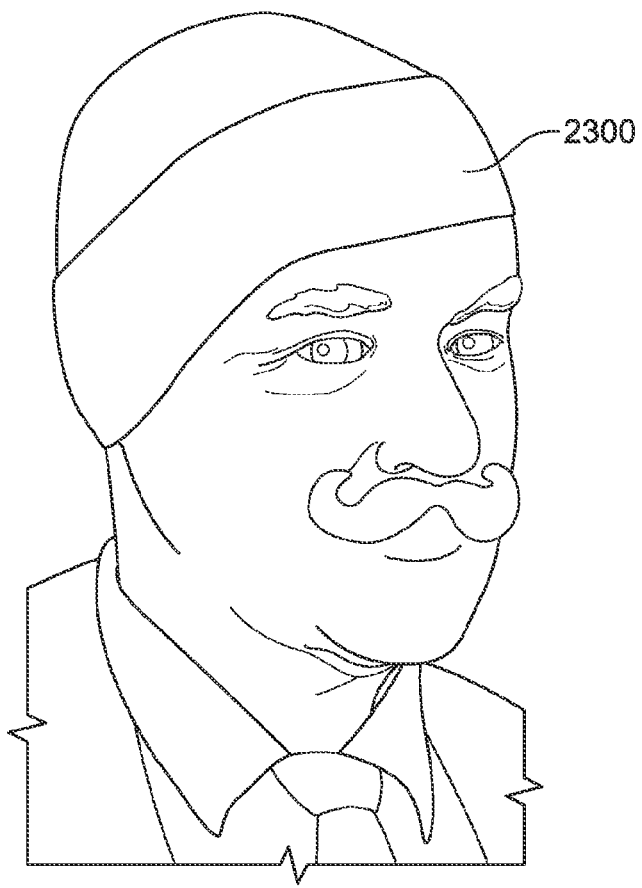
FIG. 23 depicts a user of an electronic earplug wearing a headband.

FIG. 23 depicts a user of an electronic earplug wearing a headband 2300. It has been found that wearing such a headband can reduce the effect of wind interference on the electronic earplug microphone. For example, experimental results have indicated that when wearing the headband, wind interference was acceptable up to about 35 miles per hour. Without wearing the headband, wind interference was acceptable up to about 12-15 miles per hour.

Figure 24:
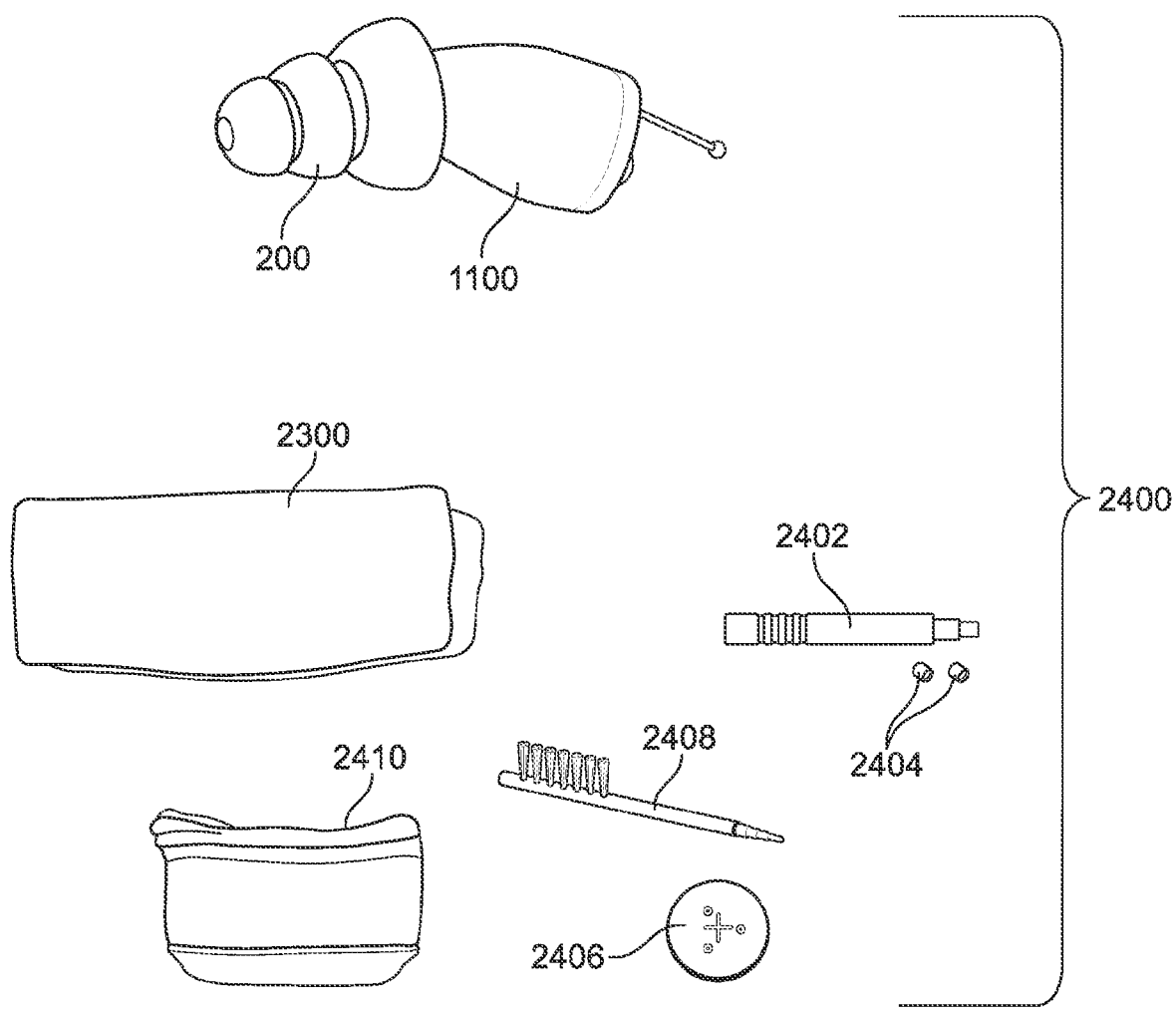
FIG. 24 depicts a kit comprising an electronic earplug and electronic earplug accessories used in accordance with embodiments of the present technology.

FIG. 24 depicts a kit 2400 comprising an electronic earplug 1100 with eartip 200 disposed thereon, headband 2300, damper replacement tool 2402, dampers 2404, battery 2406, eartip cleaning tool 2408 and pouch 2410 configured to store kit items. In an embodiment, a kit can include: two electronic earplugs, eight batteries, a damper and a damper removal tool. In certain embodiments, a kit can include other combinations of an electronic earplug and the above accessories.

While particular elements, embodiments and applications of the present invention have been shown and described, it will be understood that the invention is not limited thereto since modifications can be made by those skilled in the art without departing from the scope of the present disclosure, particularly in light of the foregoing teachings.

What is claimed is:

1. A kit including:
    an electronic earplug battery;
    a damper removal tool; and
    an electronic earplug comprising:
        a microphone configured to convert ambient sound to input electrical signals;
        a circuit operatively connected to the microphone, the circuit configured to receive the input electrical signals from the microphone and provide output electrical signals to a receiver, the circuit configured to modify a sound output level from the electronic earplug to a user's ear canal based on a sound input level of the ambient sound;
        the receiver operatively connected to the circuit, the receiver configured to convert the output electrical signals into sound that is communicated to the user's ear canal;
        a sound channel configured to communicate sound to the user's ear canal; and
        an acoustic damper disposed in the sound channel.

2. The kit of claim 1, further including a headband comprising a coil.

3. The kit of claim 1, further including an eartip.

4. The kit of claim 1, further including a pouch configured to store the other kit items.

5. The kit of claim 1, further including a second electronic earplug.

6. An electronic earplug comprising:
    a microphone configured to convert ambient sound to input electrical signals;
    a circuit operatively connected to the microphone, the circuit configured to receive the input electrical signals from the microphone and provide output electrical signals to a receiver, the circuit configured to modify a sound output level from the electronic earplug to a user's ear canal based on a sound input level of the ambient sound, wherein the circuit is configured such that for sound input levels between a first value and a second value, the sound output level is about equal to the sound input level, wherein the circuit is configured such that for sound input levels between the second value and a third value that is greater than the second value, the sound output level is equal to about the second value, and wherein the circuit is configured to reduce the second value by about 10 dB using a resistor across terminals of the receiver; and the receiver operatively connected to the circuit, the receiver configured to convert the output electrical signals into sound that is communicated to the user's ear canal.

7. The electronic earplug of claim 6, wherein the second value is about 105 dB SPL or about 115 dB SPL.

8. The electronic earplug of claim 6, wherein the circuit is configured such that for sound input levels between the first value and a fourth value that is less than the first value, the sound output level is greater than the sound input level.

9. The electronic earplug of claim 6, further comprising an eartip configured to block at least about 35 dB of the ambient sound when the eartip is received in the user's ear canal.

10. The electronic earplug of claim 6, wherein the circuit includes a battery polarity reversing circuit configured to detect the polarity of a battery and reverse polarity based on the orientation of the battery.

11. The electronic earplug of claim 6, wherein the circuit includes a Class B output.

12. The electronic earplug of claim 6, wherein the circuit includes a circuit configured to signal when battery power is below a certain level.

13. The electronic earplug of claim 6, wherein the microphone is blast resistant.

14. The electronic earplug of claim 6, wherein the electronic earplug is fully supported by the ear canal.

15. The electronic earplug of claim 6 configured to be coupled with a two-way wireless communication device such that signals received from the two-way wireless communication device are communicated to the electronic earplug.

16. The electronic earplug of claim 6 configured to be coupled with a two-way wireless communication device such that signals received at a microphone configured to receive audible cues from the wearer of the electronic earplug are transmitted from the two-way wireless communication device.

17. An electronic earplug comprising:
a microphone configured to convert ambient sound to input electrical signals;
a circuit operatively connected to the microphone, the circuit configured to receive the input electrical signals from the microphone and provide output electrical signals to a receiver, the circuit configured to modify a sound output level from the electronic earplug to a user's ear canal based on a sound input level of the ambient sound, wherein the circuit is configured such that for sound input levels between a first value and a second value, the sound output level is about equal to the sound input level, wherein the circuit is configured such that it can be switched between a first setting and a second setting, the first setting having the sound output level be about equal to the sound input level for inputs up to about the first value, the second setting having the sound output level be greater than the sound input level for inputs up to about the first value, and wherein the circuit is configured such that it can be switched between the first setting and the second setting by throwing a single pole single throw switch in series with a threshold knee controlling portion of the circuit; and the receiver operatively connected to the circuit, the receiver configured to convert the output electrical signals into sound that is communicated to the user's ear canal.

18. The electronic earplug of claim 17, further comprising an eartip configured to block at least about 35 dB of the ambient sound when the eartip is received in the user's ear canal.

19. The electronic earplug of claim 17, wherein the circuit includes a battery polarity reversing circuit configured to detect the polarity of a battery and reverse polarity based on the orientation of the battery.

20. The electronic earplug of claim 17, wherein the circuit includes a Class B output.

21. The electronic earplug of claim 17, wherein the circuit includes a circuit configured to signal when battery power is below a certain level.

22. The electronic earplug of claim 17, wherein the microphone is blast resistant.

23. The electronic earplug of claim 17, wherein the electronic earplug is fully supported by the ear canal.

24. The electronic earplug of claim 17 configured to be coupled with a two-way wireless communication device such that signals received from the two-way wireless communication device are communicated to the electronic earplug.

25. The electronic earplug of claim 17 configured to be coupled with a two-way wireless communication device such that signals received at a microphone configured to receive audible cues from the wearer of the electronic earplug are transmitted from the two-way wireless communication device.

26. An electronic earplug comprising:
a microphone configured to convert ambient sound to input electrical signals;
a circuit operatively connected to the microphone, the circuit configured to receive the input electrical signals from the microphone and provide output electrical signals to a receiver, the circuit configured to modify a sound output level from the electronic earplug to a user's ear canal based on a sound input level of the ambient sound, wherein the circuit is configured such that for sound input levels between a first value and a second value, the sound output level is about equal to the sound input level, wherein the circuit is configured such that it can be switched between a first setting and a second setting, the first setting having the sound output level be greater than the sound input level for inputs up to about the first value, the second setting having the sound output level be less than the sound input level for at least one input above the second value, and wherein the circuit is configured such that it can be switched between the first setting and the second setting by throwing a single pole double throw switch to select two different volume control resistors; and the receiver operatively connected to the circuit, the receiver configured to convert the output electrical signals into sound that is communicated to the user's ear canal.

27. The electronic earplug of claim 26, further comprising an eartip configured to block at least about 35 dB of the ambient sound when the eartip is received in the user's ear canal.

28. The electronic earplug of claim 26, wherein the circuit includes a battery polarity reversing circuit configured to detect the polarity of a battery and reverse polarity based on the orientation of the battery.

29. The electronic earplug of claim 26, wherein the circuit includes a Class B output.

30. The electronic earplug of claim 26, wherein the circuit includes a circuit configured to signal when battery power is below a certain level.

31. The electronic earplug of claim 26, wherein the microphone is blast resistant.

32. The electronic earplug of claim 26, wherein the electronic earplug is fully supported by the ear canal.

33. The electronic earplug of claim 26 configured to be coupled with a two-way wireless communication device such that signals received from the two-way wireless communication device are communicated to the electronic earplug.

34. The electronic earplug of claim 26 configured to be coupled with a two-way wireless communication device such that signals received at a microphone configured to receive audible cues from the wearer of the electronic earplug are transmitted from the two-way wireless communication device.

35. An electronic earplug comprising:
a microphone configured to convert ambient sound to input electrical signals;
a circuit operatively connected to the microphone, the circuit configured to receive the input electrical signals from the microphone and provide output electrical signals to a receiver, the circuit configured to modify a sound output level from the electronic earplug to a user's ear canal based on a sound input level of the ambient sound, wherein the circuit is configured such that for sound input levels between a first value and a second value, the sound output level is about equal to the sound input level;
the receiver operatively connected to the circuit, the receiver configured to convert the output electrical signals into sound that is communicated to the user's ear canal; and
a receive coil configured to be magnetically coupled with a remote transmit coil such that signals received from the remote transmit coil are communicated to the electronic earplug, wherein the receive coil includes a long axis that extends substantially parallel to a sound channel configured to deliver sound to a user's ear canal such that the receive coil remains similarly oriented relative to the user's ear canal when the electronic earplug is rotated in the user's ear canal.

36. The electronic earplug of claim 35, wherein the signals received from the remote transmit coil are not amplified or attenuated by the circuit prior to being converted to sound for delivery using the electronic earplug.

37. An electronic earplug comprising:
a microphone configured to convert ambient sound to input electrical signals;
a circuit operatively connected to the microphone, the circuit configured to receive the input electrical signals from the microphone and provide output electrical signals to a receiver, the circuit configured to modify a sound output level from the electronic earplug to a user's ear canal based on a sound input level of the ambient sound, wherein the circuit is configured such that for sound input levels between a first value and a second value, the sound output level is about equal to the sound input level; and
the receiver operatively connected to the circuit, the receiver configured to convert the output electrical signals into sound that is communicated to the user's ear canal,
wherein the electronic earplug includes an exterior facing end that is disposed opposite the user's ear canal when the electronic earplug is being worn, and wherein the microphone is configured to receive ambient sound through an inlet disposed on the exterior facing end.

38. The electronic earplug of claim 37, further comprising an eartip configured to block at least about 35 dB of the ambient sound when the eartip is received in the user's ear canal.

39. The electronic earplug of claim 37, wherein the microphone is blast resistant.

40. The electronic earplug of claim 37, wherein the electronic earplug is fully supported by the ear canal.

41. An electronic earplug comprising:
a microphone configured to convert ambient sound to input electrical signals;
a circuit operatively connected to the microphone, the circuit configured to receive the input electrical signals from the microphone and provide output electrical signals to a receiver, the circuit configured to modify a sound output level from the electronic earplug to a user's ear canal based on a sound input level of the ambient sound, wherein the circuit is configured such that for sound input levels between a first value and a second value, the sound output level is about equal to the sound input level; and
the receiver operatively connected to the circuit, the receiver configured to convert the output electrical signals into sound that is communicated to the user's ear canal,
wherein the electronic earplug includes an exterior facing end that is disposed opposite the user's ear canal when the electronic earplug is being worn, and wherein the microphone is configured to receive ambient sound through an inlet disposed on a side of the electronic earplug that is not the exterior facing end.

42. The electronic earplug of claim 41, further comprising an eartip configured to block at least about 35 dB of the ambient sound when the eartip is received in the user's ear canal.

43. The electronic earplug of claim 41, wherein the microphone is blast resistant.

44. The electronic earplug of claim 41, wherein the electronic earplug is fully supported by the ear canal.

45. An electronic earplug comprising:
a microphone configured to convert ambient sound to input electrical signals;
a circuit operatively connected to the microphone, the circuit configured to receive the input electrical signals from the microphone and provide output electrical signals to a receiver, the circuit configured to modify a sound output level from the electronic earplug to a user's ear canal based on a sound input level of the ambient sound, wherein the circuit is configured such that for sound input levels between a first value and a second value, the sound output level is about equal to the sound input level;
the receiver operatively connected to the circuit, the receiver configured to convert the output electrical signals into sound that is communicated to the user's ear canal;
a receive coil configured to inductively receive a first audio signal from a radio interface loop, the first audio signal being communicated from a two-way communication device operably connected to the radio interface loop; and a transmit coil configured to generate a second audio signal, wherein the radio interface loop is configured to inductively receive the second audio signal and communicate the second audio signal to the two-way communication device, wherein the second audio signal is coupled as an FM signal, and wherein the radio interface loop is connected to the two-way communication device via a radio interface module comprising a high-pass filter configured to filter the second audio signal and an FM demodulator configured to demodulate the second audio signal.

46. The electronic earplug of claim 45, wherein the transmit coil is configured to generate the second audio signal based on sound received at a boom microphone extending from a headset that includes the electronic earplug.

47. The electronic earplug of claim 45, wherein the FM signal has a center frequency of about 100 kHz.

48. The electronic earplug of claim 45, wherein the radio interface module is configured such that the second audio signal is filtered using the high pass filter before the second audio signal is demodulated using the FM demodulator.

49. The electronic earplug of claim 45, wherein the first audio signal is a baseband audio signal, and wherein the radio interface loop is connected to the two-way communication device via a radio interface module comprising a low pass filter configured to filter the first audio signal.

50. The electronic earplug of claim 45, wherein the two-way communication device is a two-way radio.

* * * * *